(12) United States Patent
Coleman et al.

(10) Patent No.: US 7,638,549 B2
(45) Date of Patent: Dec. 29, 2009

(54) MITOTIC KINESIN INHIBITORS

(75) Inventors: Paul J. Coleman, Wallingford, PA (US); Christopher D. Cox, Harleysville, PA (US)

(73) Assignee: Merck & Co. Inc., Rahway, NJ (US)

( * ) Notice: Subject to any disclaimer, the term of this patent is extended or adjusted under 35 U.S.C. 154(b) by 259 days.

(21) Appl. No.: 10/568,000

(22) PCT Filed: Aug. 11, 2004

(86) PCT No.: PCT/US2004/026242

§ 371 (c)(1), (2), (4) Date: Feb. 10, 2006

(87) PCT Pub. No.: WO2005/017190

PCT Pub. Date: Feb. 24, 2005

(65) Prior Publication Data

US 2006/0287302 A1    Dec. 21, 2006

Related U.S. Application Data

(60) Provisional application No. 60/495,466, filed on Aug. 15, 2003.

(51) Int. Cl.
*A61K 31/4025* (2006.01)
*C07D 207/09* (2006.01)
*C07D 207/20* (2006.01)

(52) U.S. Cl. .................. 514/422; 514/423; 514/428; 514/429; 546/524; 546/565; 546/571

(58) Field of Classification Search ............ 514/422, 514/423, 426, 428, 429; 548/518, 538, 557, 548/565, 577
See application file for complete search history.

(56) References Cited

U.S. PATENT DOCUMENTS

| | | | |
|---|---|---|---|
| 3,644,414 A | 2/1972 | Helsey et al. | |
| 6,057,342 A | 5/2000 | Fevig et al. | |
| 6,440,686 B1 | 8/2002 | Sakowicz | |
| 7,235,580 B2 * | 6/2007 | Breslin et al. | 514/422 |

FOREIGN PATENT DOCUMENTS

| | | |
|---|---|---|
| EP | 0 418 845 | 8/1995 |
| WO | WO 93/20099 | 10/1993 |
| WO | WO 98/06694 | 2/1998 |
| WO | WO 03/049527 | 6/2003 |
| WO | WO 03/105855 | 12/2003 |
| WO | WO 03/106417 | 12/2003 |
| WO | WO 2004/037171 | 5/2004 |
| WO | WO 2005/019205 | 3/2005 |
| WO | WO 2005/019206 | 3/2005 |

OTHER PUBLICATIONS

Patani et al. Chem. Rev., 1996, 96, 3147-49.*
C. Sonesson, et al., J. Org. Chem. 1996, vol. 61, pp. 4756-4763.
N. Iwasawa, et al., J. Org. Chem. 1998, vol. 63, pp. 3164-3165.
N. Iwasawa, et al., J. Org. Chem. 1997, vol. 62, pp. 1918-1919.
R. Mison, et al., J. Chem. Research(S), 1989, 126-127.
O. Yebdri, et al., Bulletin De La Societe Chimique de France, 1983, pp. 195-201.
A. Ranjon, Bulletin De La Societe Chimique de France, 1971, pp. 2068-2072.
M. Bujard, et al., Tetrahedron Letters, vol. 40, 1999, pp. 8785-8788.
M. Carpes, et al., Synlett, No. 7, 2000, pp. 1037-1039.
A. Boukhari, et al., J. Cryst. Spect. Res., vol. 19, Iss. 3, 1989, pp. 603-621.
C. Cox, et al., Bioorganic & Medicinal Chem Ltrs. vol. 15, pp. 2041-2045 (2005).
W. Tao, Cell Cycle, vol. 4(11), pp. 1495-1499 (2005).
K. D. Chu, et al., Proc. Am. Soc. Clin. Oncol., abstract 525, pp. 131 (2003).
R. Sakowicz, et al., Cancer Research, vol. 64, pp. 3276-3280 (2004).
W. Tao, et al., Cancer Cell, vol. 8, pp. 49-59 (2005).
M. Fraley, et al., Bioorganic & Medicinal Chem Ltrs., vol. 16, pp. 1775-1779 (2006).
R. Garbaccio, et al., Bioorganic & Medicinal Chem Ltrs., vol. 16, pp. 1780-1783 (2006).
C. Cox, et al., Bioorganic & Medicinal Chem Ltrs., vol. 16, 3175-3179 (2006).
Cox, CD et al., J. Med Chem., vol. XX, pp. XX-XX, (2008), "Kinesin spindle protein (KSP) inhibitors. Part 9: The discovery of KSP inhibitor MK-0731 for the treatment of taxane-refractory cancer".

* cited by examiner

*Primary Examiner*—Kamal Saeed
*Assistant Examiner*—Yong Chu
(74) *Attorney, Agent, or Firm*—Nicole M. Beeler; David A. Muthard

(57) ABSTRACT

The present invention relates to dihydropyrrole compounds that are useful for treating cellular proliferative diseases, for treating disorders associated with KSP kinesin activity, and for inhibiting KSP kinesin. The invention is also related to compositions which comprise these compounds, and methods of using them to treat cancer in mammals.

3 Claims, No Drawings

MITOTIC KINESIN INHIBITORS

PRIORITY CLAIM

This application is a §371 application of PCT/US2004/026242 that was filed on Aug. 11, 2005, which claims priority from the U.S. Provisional Application Nos. 60/495,466, filed on Aug. 15, 2003, now expired.

BACKGROUND OF THE INVENTION

This invention relates to 2,2-disubstituted 2,5-dihydropyrrole derivatives that are inhibitors of mitotic kinesins, in particular the mitotic kinesin KSP, and are useful in the treatment of cellular proliferative diseases, for example cancer, hyperplasias, restenosis, cardiac hypertrophy, immune disorders and inflammation.

Among the therapeutic agents used to treat cancer are the taxanes and vinca alkaloids. Taxanes and vinca alkaloids act on microtubules, which are present in a variety of cellular structures. Microtubules are the primary structural element of the mitotic spindle. The mitotic spindle is responsible for distribution of replicate copies of the genome to each of the two daughter cells that result from cell division. It is presumed that disruption of the mitotic spindle by these drugs results in inhibition of cancer cell division, and induction of cancer cell death. However, microtubules form other types of cellular structures, including tracks for intracellular transport in nerve processes. Because these agents do not specifically target mitotic spindles, they have side effects that limit their usefulness.

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms. Examples of this include not only the taxanes, but also the camptothecin class of topoisomerase I inhibitors. From both of these perspectives, mitotic kinesins are attractive targets for new anti-cancer agents.

Mitotic linesins are enzymes essential for assembly and function of the mitotic spindle, but are not generally part of other microtubule structures, such as in nerve processes. Mitotic linesins play essential roles during all phases of mitosis. These enzymes are "molecular motors" that transform energy released by hydrolysis of Al? into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the mitotic kinesins which have been identified is KSP. KSP belongs to an evolutionarily conserved kinesin subfamily of plus end-directed microtubule motors that assemble into bipolar homotetramers consisting of antiparallel homodimers. During mitosis KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described [Blangy, et al., Cell, 83:1159-69 (1995); Whitehead, et al., Arthritis Rheum., 39:1635-42 (1996); Galgio et al., J. Cell Biol., 135:339-414 (1996); Blangy, et al., J Biol. Chem., 272:19418-24 (1997); Blangy, et al., Cell Motil Cytoskeleton, 40:174-82 (1998); Whitehead and Rattner, J. Cell Sci., 111:2551-61 (1998); Kaiser, et al., JBC 274:18925-31 (1999); GenBank accession numbers: X85137, NM004523 and U37426], and a fragment of the KSP gene (TRIP5) has been described [Lee, et al., Mol Endocrinol., 9:243-54 (1995); GenBank accession number L40372]. Xenopus KSP homologs (Eg5), as well as Drosophila K-LP61 F/KRP 130 have been reported.

Certain quinazolinones have recently been described as being inhibitors of KSP (PCT Publ. WO 01/30768, May 3, 2001).

Mitotic kinesins are attractive targets for the discovery and development of novel mitotic chemotherapeutics. Accordingly, it is an object of the present invention to provide compounds, methods and compositions useful in the inhibition of KSP, a mitotic kinesin.

SUMMARY OF THE INVENTION

The present invention relates to dihydropyrrole derivatives, that are useful for treating cellular proliferative diseases, for treating disorders associated with KSP kinesin activity, and for inhibiting KSP kinesin. The compounds of the invention may be illustrated by the Formula I:

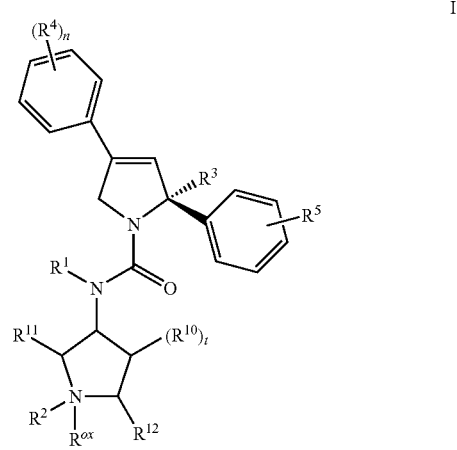

DETAILED DESCRIPTION OF THE INVENTION

The compounds of this invention are useful in the inhibition of mitotic kinesins and are Illustrated by a compound of Formula I:

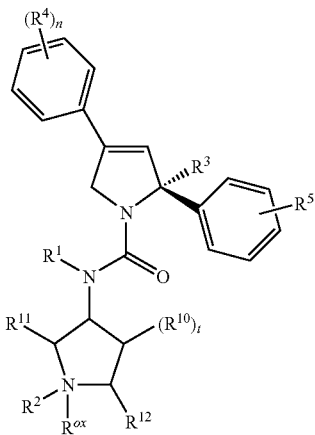

or a pharmaceutically acceptable salt or stereoisomer thereof,
wherein:
a is 0 or 1;
b is 0 or 1;
m is 0, 1, or 2;
n is 0, 1, 2 or 3;
r is 0 or 1;
s is 0 or 1;
t is 0, 1 or 2;
$R^1$ and $R^2$ are independently selected from: H, $(C_1-C_6)$alkyl, aryl, heterocyclyl and $(C_3-C_6)$cycloalkyl, optionally substituted with one, two or three substituents selected from $R^7$;
$R^3$ is selected from:
  1) hydrogen;
  2) $C_1-C_{10}$ alkyl;
  3) $C_1-C_{10}$ alkyl-O—$R^d$,
  4) $C_2-C_{10}$ alkenyl-O—$R^d$,
  5) $C_2-C_{10}$ alkenyl-O—$R^d$,
  6) $(C_1-C_6$-alkylene$)_n C_3-C_8$ cycloalkyl-O—$R^d$,
  7) $C_1-C_{10}$ alkyl-$(C=O)_b$—$NR^cR^{c1}$,
  8) $C_2-C_{10}$ alkenyl-$(C=O)_b NR^cR^{c1}$,
  9) $C_2-C_{10}$ alkynyl-$(C=O)_b NR^cR^{c1}$,
  10) $(C_1-C_6$-alkylene$)_n C_3-C_8$ cycloalkyl-$(C=O)_b NR^cR^{c1}$,
  11) $C_1-C_{10}$ alkyl-$S(O)_m$—$R^d$,
  12) $C_2-C_{10}$ alkenyl-$S(O)_m$—$R^d$,
  13) $C_2-C_{10}$ alkynyl-$S(O)_m$—$R^d$,
  14) $(C_1-C_6$-alkylene$)_n C_3-C_8$ cycloalkyl-$S(O)_m$—$R^d$,
said alkyl, alkenyl, alkynyl and cycloalkyl are optionally substituted with one or more substituents selected from $R^6$;
$R^4$ is independently selected from:
  1) $(C=O)_a O_b C_1-C_{10}$ alkyl,
  2) $(C=O)_a O_b$aryl,
  3) $CO_2H$,
  4) halo,
  5) CN,
  6) OH,
  7) $O_b C_1-C_6$ perfluoroalkyl,
  8) $O_a(C=O)_b NR^8R^9$,
  9) $S(O)_m R^a$,
  10) $S(O)_2 NR^8R^9$,
said alkyl, aryl, alkenyl, alkynyl, heterocyclyl, and cycloalkyl optionally substituted with one, two or three substituents selected from $R^7$;
$R^5$ is selected from:
  1) hydrogen;
  2) $(C=O)_a O_b C_1-C_{10}$ alkyl,
  3) $(C=O)_a O_b$aryl,
  4) $CO_2H$,
  5) halo,
  6) CN,
  7) OH,
  8) $O_b C_1-C_6$ perfluoroalkyl,
  9) $O_a(C=O)_b NR^8R^9$,
  10) $S(O)_m R^a$,
  11) $S(O)_2 NR^8R^9$,
said alkyl, aryl, alkenyl, alkynyl, heterocyclyl, and cycloalkyl optionally substituted with one, two or three substituents selected from $R^7$;
$R^6$ is independently selected from:
  1) $(C=O)_a O_b C_1-C_{10}$ alkyl,
  2) $(C=O)_a O_b$aryl,
  3) $C_2-C_{10}$ alkenyl,
  4) $C_2-C_{10}$ alkynyl,
  5) $(C=O)_a O_b$ heterocyclyl,
  7) halo,
  8) CN,
  9) OH,
  10) $O_b C_1-C_6$ perfluoroalkyl
  11) $O_a(C=O)_b NR^8R^9$,
  12) $S(O)_m R^a$,
  13) $S(O)_2 NR^8R^9$,
  14) oxo,
  15) CHO,
  16) $(N=O)R^8R^9$, or
  17) $(C=O)_a O_b C_3-C_8$ cycloalkyl,
said alkyl, aryl, alkenyl, alkynyl, heterocyclyl, and cycloalkyl optionally substituted with one, two or three substituents selected from $R^7$;
$R^7$ is selected from:
  1) $(C=O)_r O_s (C_1-C_{10})$alkyl,
  2) $O_r(C_1-C_3)$perfluoroalkyl,
  3) oxo,
  4) OH,
  5) halo,
  6) CN,
  7) $(C_2-C_{10})$alkenyl,
  8) $(C_2-C_{10})$alkyl,
  9) $(C=O)_r O_s(C_3-C_6)$cycloalkyl,
  10) $(C=O)_r O_s(C_0-C_6)$alkylene-aryl,
  11) $(C=O)_r O_s(C_0-C_6)$alkylene-heterocyclyl,
  12) $(C=O)_r O_s(C_0-C_6)$alkylene-$N(R^b)_2$,
  13) $C(O)R^a$,
  14) $(C_0-C_6)$alkylene-$CO_2R^a$,
  15) $C(O)H$,
  16) $(C_0-C_6)$alkylene-$CO_2H$, and
  17) $C(O)N(R^b)_2$,
  18) $S(O)_m R^a$, and
  19) $S(O)_2 N(R^b)_2$;
said alkyl, alkenyl, alkynyl, cycloalkyl, aryl, alkylene and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, $NO_2$ and $N(R^b)_2$;
$R^8$ and $R^9$ are independently selected from:
  1) H,
  2) $(C=O)O_b C_1-C_{10}$ alkyl,
  3) $(C=O)O_b C_3-C_8$ cycloalkyl,
  4) $(C=O)O_b$aryl,
  5) $(C=O)O_b$heterocyclyl, 6) $C_1$-$C_{10}$ alkyl,
7) aryl,
8) $C_2$-$C_{10}$ alkenyl,
9) $C_2$-$C_{10}$ alkynyl,
10) heterocyclyl,
11) $C_3$-$C_8$ cycloalkyl,
12) $SO_2R^a$, and
13) (C=O)$NR^b{}_2$, said alkyl, cycloalkyl, aryl, heterocylyl, alkenyl, and alkynyl is optionally substituted with one, two or three substituents selected from $R^7$, or $R^8$ and $R^9$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;

$R^{10}$ is selected from: F and —$CH_2F$;

$R^{11}$ and $R^{12}$ are independently selected from: H and —$CH_2F$;

$R^{ox}$ is absent or is oxo;

$R^a$ is independently selected from: ($C_1$-$C_6$)alkyl, ($C_3$-$C_6$)cycloalkyl, aryl, or heterocyclyl, optionally substituted with one, two or three substituents selected from $R^7$;

$R^b$ is independently selected from: H, ($C_1$-$C_6$)alkyl, aryl, heterocyclyl, ($C_3$-$C_6$)cycloalkyl, (C=O)O$C_1$-$C_6$alkyl, (C=O)$C_1$-$C_6$ alkyl, (C=O)aryl, (C=O)heterocyclyl, (C=O)$NR^eR^{e_1}$ or $S(O)_2R^a$, optionally substituted with one, two or three substituents selected from $R^7$;

$R^c$ and $R^{c_1}$ are independently selected from H, ($C_1$-$C_6$)alkyl, aryl, $NH_2$, OH, $OR^a$, —($C_1$-$C_6$)alkyl-OH, —($C_1$-$C_6$)alkyl-O—($C_1$-$C_6$)alkyl, (C=O)O$C_1$-$C_6$ alkyl, (C=O)$C_1$-$C_6$ alkyl, (C=O)aryl, (C=O)heterocyclyl, (C=O)$NR^eR^{e_1}$, $S(O)_2R^a$ and —($C_1$-$C_6$)alkyl-N($R^b)_2$, wherein the alkyl is optionally substituted with one, two or three substituents selected from $R^7$; or $R^c$ and $R^{c_1}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;

$R^d$ is selected from: H, ($C_1$-$C_6$)alkyl, —($C_2$-$C_6$)alkyl-OH, —($C_1$-$C_6$)alkyl-O—($C_1$-$C_6$)alkyl and —($C_1$-$C_6$)alkyl-N($R^b)_2$, wherein the allyl is optionally substituted with one, two or three substituents selected from $R^7$;

$R^e$ and $R^{e_1}$ are independently selected from; H, ($C_1$-$C_6$)alkyl, aryl, heterocyclyl and ($C_3$-$C_6$)cycloalkyl, optionally substituted with one, two or three substituents selected from $R^7$; or $R^e$ and $R^{e_1}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$.

The compounds of this invention are useful in the inhibition of mitotic kinesins and are illustrated by a compound of Formula II:

or a pharmaceutically acceptable salt or stereoisomer thereof, wherein:

a is 0 or 1;
b is 0 or 1;
m is 0, 1, or 2;
n is 0, 1, 2 or 3;
r is 0 or 1;
s is 0 or 1;
t is 0 or 1;

$R^1$ and $R^2$ are independently selected from: H, ($C_1$-$C_6$)alkyl, aryl, heterocyclyl and ($C_3$-$C_6$)cycloalkyl, optionally substituted with one, two or three substituents selected from $R^7$;

$R^3$ is selected from:
 1) hydrogen;
 2) $C_1$-$C_{10}$ alkyl;
 3) $C_1$-$C_{10}$ alkyl-O—$R^d$,
 4) $C_2$-$C_{10}$ alkenyl-O—$R^d$,
 5) $C_2$-$C_{10}$ alkynyl-O—$R^d$,
 6) ($C_1$-$C_6$-alkylene)$_n C_3$-$C_8$ cycloalkyl-O—$R^d$,
 7) $C_1$-$C_{10}$ alkyl-C=O)$_b$—$NR^cR^{c_1}$,
 8) $C_2$-$C_{10}$ alkenyl-(C=O)$_b NR^cR^{c_1}$,
 9) $C_2$-$C_{10}$ alkynyl-(C=O)$_b NR^cR^{c_1}$,
 10) ($C_1$-$C_6$-alkylene)$_n C_3$-$C_8$ cycloalkyl(C=O)$_b NR^cR^{c_1}$,
 11) $C_1$-$C_{10}$ alkyl-S(O)$_m$—$R^d$,
 12) $C_2$-$C_{10}$ alkenyl-S(O)$_m$—$R^d$,
 13) $C_2$-$C_{10}$ alkynyl-S(O)$_m$—$R^d$,
 14) ($C_1$-$C_6$-alkylene)$_n C_3$-$C_8$ cycloalkyl-S(O)$_m$—$R^d$, said alkyl, alkenyl, alkynyl and cycloalkyl are optionally substituted with one or more substituents selected from $R^6$;

$R^4$ is independently selected from.
 1) (C=O)$_a O_b C_1$-$C_{10}$ alkyl,
 2) (C-O)$_a O_b$aryl,
 3) $CO_2H$,
 4) halo,
 5) CN,
 6) OH,
 7) $O_b C_1$-$C_6$ perfluoroalkyl,
 8) $O_a$(C=O)$_b NR^8R^9$,
 9) S(O)$_m R^a$,
 10) S(O)$_2 NR^8R^9$, said alkyl, aryl, alkenyl, alkynyl, heterocyclyl, and cycloalkyl optionally substituted with one, two or three substituents selected from $R^7$;

$R^5$ is selected from:
1) hydrogen;
2) $(C=O)_aO_bC_1$-$C_{10}$ alkyl,
3) $(C=O)_aO_b$aryl,
4) $CO_2H$,
5) halo,
6) CN,
7) OH,
8) $O_bC_1$-$C_6$ perfluoroalkyl,
9) $O_a(C=O)_bNR^8R^9$,
10) $S(O)_mR^a$,
11) $S(O)_2NR^8R^9$, said alkyl, aryl, alkenyl, alkynyl, heterocyclyl, and cycloalkyl optionally substituted with one, two or three substituents selected from $R^7$;

$R^6$ is independently selected from:
1) $(C=O)_aO_bC_1$-$C_{10}$ alkyl,
2) $(C=O)_aO_b$aryl,
3) $C_2$-$C_{10}$ alkenyl,
4) $C_2$-$C_{10}$ alkynyl,
5) $(C=O)_aO_b$ heterocyclyl,
6) $CO_2H$,
7) halo,
8) CN,
9) OH,
10) $O_bC_1$-$C_6$ perfluoroalkyl,
11) $O_a(C=O)_bNR^8R^9$,
12) $S(O)_mR^a$,
13) $S(O)_2NR^8R^9$,
14) oxo,
15) CHO,
16) $(N=O)R^8R^9$, or
17) $(C=O)_aO_bC_3$-$C_8$ cycloalkyl, said alkyl, aryl, alkenyl, alkynyl, heterocyclyl, and cycloalkyl optionally substituted with one, two or three substituents selected from $R^7$;

$R^7$ is selected from:
1) $(C=O)_rO_s(C_1$-$C_{10})$alkyl,
2) $O_r(C_1$-$C_3)$perfluoroalkyl,
3) oxo,
4) OH,
5) halo,
6) CN,
7) $(C_2$-$C_{10})$alkenyl,
8) $(C_2$-$C_{10})$alkynyl,
9) $(C=O)_rO_s(C_3$-$C_6)$cycloalkyl,
10) $(C=O)_rO_s(C_0$-$C_6)$alkylene-aryl,
11) $(C=O)_rO_s(C_0$-$C_6)$alkylene-heterocyclyl,
12) $(C=O)_rO_s(C_0$-$C_6)$alkylene-$N(R^b)_2$,
13) $C(O)R^a$,
14) $(C_0$-$C_6)$alkylene-$CO_2R^a$,
15) C(O)H,
16) $(C_0$-$C_6)$alkylene-$CO_2H$, and
17) $C(O)N(R^b)_2$,
18) $S(O)_mR^a$, and
19) $S(O)_2N(R^b)_2$;

said alkyl, alkenyl, alkynyl, cycloalkyl, aryl, alkylene and heterocyclyl is optionally substituted with up to three substituents selected from $R^b$, OH, $(C_1$-$C_6)$alkoxy, halogen, $CO_2H$, CN, $O(C=O)C_1$-$C_6$ alkyl, oxo, $NO_2$ and $N(R^b)_2$;

$R^8$ and $R^9$ are independently selected from:
1) H,
2) $(C=O)O_bC_1$-$C_{10}$ alkyl,
3) $(C=O)O_bC_3$-$C_8$ cycloalkyl,
4) $(C=O)O_b$aryl,
5) $(C=O)O_b$heterocyclyl,
6) $C_1$-$C_{10}$ alkyl,
7) aryl,
8) $C_2$-$C_{10}$ alkenyl,
9) $C_2$-$C_{10}$ alkynyl,
10) heterocyclyl,
11) $C_3$-$C_8$ cycloalkyl,
12) $SO_2R^a$, and
13) $(C=O)NR^b_2$, said alkyl, cycloalkyl, aryl, heterocylyl, alkenyl, and alkynyl is optionally substituted with one, two or three substituents selected from $R^7$, or $R^8$ and $R^9$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;

$R^{10}$ is selected from: F and —$CH_2F$;

$R^{12}$ is selected from: H and —$CH_2F$, provided that when t is 1, $R^{12}$ is H;

$R^{ox}$ is absent or is oxo;

$R^a$ is independently selected from; $(C_1$-$C_6)$alkyl, $(C_3$-$C_6)$cycloalkyl, aryl, or heterocyclyl, optionally substituted with one, two or three substituents selected from $R^7$;

$R^b$ is independently selected from: H, $(C_1$-$C_6)$alkyl, aryl, heterocyclyl, $(C_3$-$C_6)$cycloalkyl, $(C=O)OC_1$-$C_6$ alkyl, $(C=O)C_1$-$C_6$ alkyl, $(C=O)$aryl, $(C=O)$heterocyclyl, $(C=O)NR^eR^{e_1}$ or $S(O)_2R^a$, optionally substituted with one, two or three substituents selected from $R^7$;

$R^c$ and $R^{c_1}$ are independently selected from: H, $(C_1$-$C_6)$alkyl, aryl, $NH_2$, OH, $OR^a$, —$(C_1$-$C_6)$alkyl-OH, —$(C_1$-$C_6)$alkyl-O—$(C_1$-$C_6)$alkyl, $(C=O)OC_1$-$C_6$ alkyl, $(C=O)C_1$-$C_6$ alkyl, $(C=O)$aryl, $(C=O)$heterocyclyl, $(C=O)NR^eR^{e_1}$, $S(O)_2R^a$ and —$(C_1$-$C_6)$alkyl-$N(R^b)_2$, wherein the alkyl is optionally substituted with one, two or three substituents selected from $R^7$; or $R^c$ and $R^{c_1}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;

$R^d$ is selected from: H, $(C_1$-$C_6)$alkyl, —$(C_2$-$C_6)$alkyl-OH, —$(C_1$-$C_6)$alkyl-O—$C_1$-$C_6)$alkyl and —$(C_1$-$C_6)$alkyl-$N(R^b)_2$, wherein the alkyl is optionally substituted with one, two or three substituents selected from $R^7$;;

$R^e$ and $R^{e_1}$ are independently selected from H, $(C_1$-$C_6)$alkyl, aryl, heterocyclyl and $(C_3$-$C_6)$cycloalkyl, optionally substituted with one, two or three substituents selected from $R^7$; or $R^e$ and $R^{e_1}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$.

In an embodiment of the invention the compounds are illustrated by a compound of Formula III:

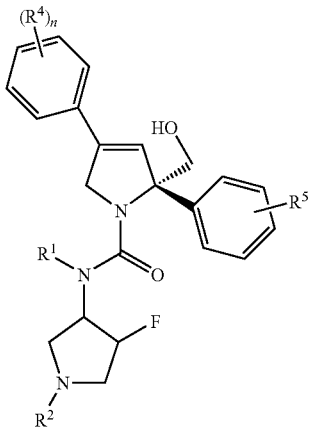

or a pharmaceutically acceptable salt or stereoisomer thereof, wherein:
a is 0 or 1;
b is 0 or 1;
m is 0, 1, or 2;
n is 0, 1 or 2;
r is 0 or 1;
s is 0 or 1;
$R^1$ and $R^2$ are independently selected from: H, $(C_1\text{-}C_6)$alkyl, aryl and $(C_3\text{-}C_6)$cycloalkyl, optionally substituted with one, two or three substituents selected from $R^7$;
$R^4$ is independently selected from:
  1) halo,
  2) OH,
  3) $O_bC_1\text{-}C_6$ perfluoroalkyl,
$R^5$ is selected from:
  1) hydrogen,
  2) halo,
  3) OH,
  4) $O_bC_1\text{-}C_6$ perfluoroalkyl,
$R^7$ is selected from:
  1) $(C=O)_rO_s(C_1\text{-}C_{10})$alkyl,
  2) $O_r(C_1\text{-}C_3)$perfluoroalkyl,
  3) oxo,
  4) OH,
  5) halo,
  6) CN,
  7) $(C_2\text{-}C_{10})$alkenyl,
  8) $(C_2\text{-}C_{10})$alkynyl,
  9) $(C=O)_rO_s(C_3\text{-}C_6)$cycloalkyl,
  10) $(C=O)_rO_s(C_0\text{-}C_6)$alkylene-aryl,
  11) $(C=O)_rO_s(C_0\text{-}C_6)$alkylene-heterocyclyl,
  12) $(C\text{-}O)_rO_s(C_0\text{-}C_6)$alkylene-N$(R^b)_2$,
  13) $C(O)R^a$,
  14) $(C_0\text{-}C_6)$alkylene-$CO_2R^a$,
  15) C(O)H,
  16) $(C_0\text{-}C_6)$alkylene-$CO_2H$, and
  17) $C(O)N(R^b)_2$,
  18) $S(O)_mR^a$, and
  19) $S(O)_2N(R^b)_2$;
said allyl, alkenyl, alkynyl, cycloalkyl, aryl, alkylene and heterocyclyl is optionally substituted with up to three substituents selected from $R^b$, OH, $(C_1\text{-}C_6)$alkoxy, halogen, $CO_2H$, CN, $O(C=O)C_1\text{-}C_6$ alkyl, oxo, $NO_2$ and $N(R^b)_2$;
$R^8$ and $R^9$ are independently selected from:
  1) H,
  2) $(C=O)O_bC_1\text{-}C_{10}$ alkyl,
  3) $(C=O)O_bC_3\text{-}C_8$ cycloalkyl,
  4) $(C=O)O_b$aryl,
  5) $(C=O)O_b$heterocyclyl,
  6) $C_1\text{-}C_{10}$ alkyl,
  7) aryl,
  8) $C_2\text{-}C_{10}$ alkenyl,
  9) $C_2\text{-}C_{10}$ alkynyl,
  10) heterocyclyl,
  11) $C_3\text{-}C_8$ cycloalkyl,
  12) $SO_2R^a$, and
  13) $(C=O)NR^b{}_2$, said alkyl, cycloalkyl, aryl, heterocylyl, alkenyl, and alkynyl is optionally substituted with one, two or three substituents selected from $R^7$, or
$R^8$ and $R^9$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;
$R^a$ is independently selected from: $(C_1\text{-}C_6)$alkyl, $(C_3\text{-}C_6)$cycloalkyl, aryl, or heterocyclyl, optionally substituted with one, two or three substituents selected from $R^7$;
$R^b$ is independently selected from: H, $(C_1\text{-}C_6)$alkyl, aryl, heterocyclyl, $(C_3\text{-}C_6)$cycloalkyl, $(C=O)OC_1\text{-}C_6$ alkyl, $(C=O)C_1\text{-}C_6$ alkyl, $(C=O)$aryl, $(C=O)$heterocyclyl, $(C=O)NR^cR^{c1}$ or $S(O)_2R^a$, optionally substituted with one, two or three substituents selected from $R^7$;
$R^c$ and $R^{c1}$ are independently selected from: H, $(C_1\text{-}C_6)$alkyl, aryl, $NH_2$, OH, $OR^a$, $-(C_1\text{-}C_6)$alkyl-OH, $-(C_1\text{-}C_6)$alkyl-O$-(C_1\text{-}C_6)$alkyl, $(C=O)OC_1\text{-}C_6$ alkyl, $(C=O)C_1\text{-}C_6$ alkyl, $(C=O)$aryl, $(C=O)$heterocyclyl, $(C=O)NR^eR^{e1}$, $S(O)_2R^a$ and $-(C_1\text{-}C_6)$alkyl-N$(R^b)_2$, wherein the alkyl is optionally substituted with one, two or three substituents selected from $R^7$; or
$R^c$ and $R^{c1}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;
$R^e$ and $R^{e1}$ are independently selected from: H. $(C_1\text{-}C_6)$alkyl, aryl, heterocyclyl and $(C_3\text{-}C_6)$cycloalkyl, optionally substituted with one, two or three substituents selected from $R^7$; or
$R^e$ and $R^{e1}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$.

Another embodiment of the present invention is illustrated by a compound of Formula IV:

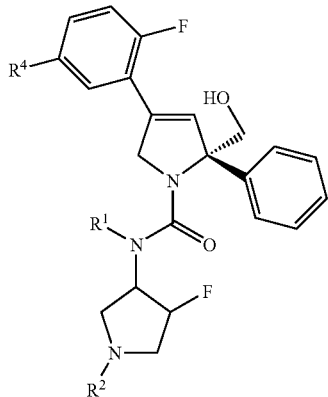

or a pharmaceutically acceptable salt or stereoisomer thereof,
wherein:
a is 0 or 1;
b is 0 or 1;
m is 0, 1, or 2;
r is 0 or 1;
s is 0 or 1;
$R^1$ and $R^2$ are independently selected from H and $(C_1-C_6)$ alkyl, optionally substituted with one, two or three substituents selected from $R^7$;
$R^4$ is independently selected from:
  1) halo,
  2) OH,
  3) $O_bC_1-C_6$ perfluoroalkyl,
$R^7$ is selected from:
  1) $(C=O)_rO_s(C_1-C_{10})$alkyl,
  2) $O_r(C_1-C_3)$perfluoroalkyl,
  3) oxo,
  4) OH,
  5) halo,
  6) CN,
  7) $(C_2-C_{10})$alkenyl,
  8) $(C_2-C_{10})$alkynyl,
  9) $(C=O)_rO_s(C_3-C_6)$cycloalkyl,
  10) $(C=O)_rO_s(C_0-C_6)$alkylene-aryl,
  11) $(C=O)_rO_s(C_0-C_6)$alkylene-heterocyclyl,
  12) $(C=O)_rO_s(C_0-C_6)$alkylene-N$(R^b)_2$,
  13) $C(O)R^a$,
  14) $(C_0-C_6)$alkylene-$CO_2R^a$,
  15) C(O)H,
  16) $(C_0-C_6)$alkylene-$CO_2H$, and
  17) $C(O)N(R^b)_2$,
  18) $S(O)_mR^a$, and
  19) $S(O)_2N(R^b)_2$;
said alkyl, alkenyl, alkynyl, cycloalkyl, aryl, alkylene and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, $NO_2$ and $N(R^b)_2$;
$R^8$ and $R^9$ are independently selected from:
  1) H,
  2) $(C=O)O_bC_1-C_{10}$ alkyl,
  3) $(C=O)O_bC_3-C_8$ cycloalkyl,
  4) $(C=O)O_baryl$,
  5) $(C=O)O_bheterocyclyl$,
  6) $C_1-C_{10}$ alkyl,
  7) aryl,
  8) $C_2-C_{10}$ alkenyl,
  9) $C_2-C_{10}$ alkynyl,
  10) heterocyclyl,
  11) $C_3-C_8$ cycloalkyl,
  12) $SO_2R^a$, and
  13) $(C=O)NR^b_2$, said alkyl, cycloalkyl, aryl, heterocylyl, alkenyl, and alkynyl is optionally substituted with one, two or three substituents selected from $R^7$, or
$R^8$ and $R^9$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;
$R^a$ is independently selected from: $(C_1-C_6)$alkyl, $(C_3-C_6)$cycloalkyl, aryl, or heterocyclyl, optionally substituted with one, two or three substituents selected from $R^7$;
$R^b$ is independently selected from: H, $(C_1-C_6)$alkyl, aryl, heterocyclyl, $(C_3-C_6)$cycloalkyl, $(C=O)OC_1-C_6$ alkyl, $(C=O)C_1-C_6$ alkyl, $(C=O)$aryl, $(C=O)$heterocyclyl, $(C=O)NR^cR^{c_1}$ or $S(O)_2R^a$, optionally substituted with one, two or three substituents selected from $R^7$;
$R^c$ and $R^{c_1}$ are independently selected from H, $(C_1-C_6)$alkyl, aryl, $NH_2$, OH, $OR^a$, —$(C_1-C_6)$alkyl-OH, —$(C_1-C_6)$alkyl-O—$(C_1-C_6)$alkyl, $(C=O)OC_1-C_6$ alkyl, $(C=O)C_1-C_6$ alkyl, $(C=O)$aryl, $(C=O)$heterocyclyl, $(C=O)NR^eR^{e_1}$, $S(O)_2R^a$ and —$(C_1-C_6)$alkyl-$N(R^b)_2$, wherein the alkyl is optionally substituted with one, two or three substituents selected from $R^7$; or
$R^c$ and $R^{c_1}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$;
$R^e$ and $R^{e_1}$ are independently selected from: H, $(C_1-C_6)$alkyl, aryl, heterocyclyl and $(C_3-C_6)$cycloalkyl, optionally substituted with one, two or three substituents selected from $R^7$; or
$R^e$ and $R^{e_1}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^7$.

Specific examples of the compounds of the instant invention include:
(2S)-4-(2,5-Difluorophenyl)-N-[(3R,4R)-4-fluoropyrrolidin-3-yl]-2-(hydroxymethyl)N-phenyl-2,5-dihydro-1H-pyrrole-1-carboxamide
(2S)-4-(2,5-Difluorophenyl)-N-[(3 S,4S)-4-fluoropyrrolidin-3 -yl]-2-(hydroxymethyl)N-phenyl-2,5-dihydro-1H-pyrrole-1-carboxamide
(2S)-4-(2,5-Difluorophenyl)-N-[(3R,4R)-4-fluoro-1-methylpyrrolidin-3-yl]-2-(hydroxymethyl)-N-phenyl-2,5-dihydro-1H-pyrrole-1-carboxamide
(2S)-4-2,5-Difluorophenyl)-N-[(3S,4S)-4-fluoro-1-methylpyrrolidin-3-yl]-2-hydroxymethyl)N-phenyl-2,5-dihydro-1H-pyrrole-1-carboxamide (2S)-4-(2,5-Difluorophenyl)-N-[(3S,5S)-5-fluoromethyl)-pyrrolidin-3-yl]-2-(hydroxymethyl)-N-methyl-2-phenyl-2,5-dihydro-1H-pyrrole-1-carboxamide (2S)-4-(2,5-Difluorophenyl)-N-[(3S,5S)-5-(fluoromethyl)-1-methylpyrrolidin-3-yl]-2-(hydroxymethyl)-N-methyl-2-phenyl-2,5-dihydro-1H-pyrrole-1-carboxamide (2S)-4-(2,5-Difluorophenyl)-N-[(3S,5R)-5-fluoromethyl)-pyrrolidin-3-yl]-2-(hydroxymethyl)-N-methyl-2-phenyl-2,5-dihydro-1H-pyrrole-1-carboxamide (2S)-4-(2,5-Difluorophenyl)-N-[(3S,5R)-5-(fluoromethyl)-1-methylpyrrolidin-3-yl]-2-(hydroxymethyl)-N-methyl-2-phenyl-2,5-dihydro-1H-pyrrole-1-carboxamide or a pharmaceutically acceptable salt or stereoisomer thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

When any variable (e.g. $R^4$, $R^7$, $R^{10}$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "alkylene" means a hydrocarbon diradical group having the specified number of carbon atoms. For example, "alkylene" includes —$CH_2$—, —$CH_2CH_2$— and the like.

When used in the phrases "$C_1$-$C_6$ aralkyl" and "$C_1$-$C_6$ heteroaralkyl" the term "$C_1$-$C_6$" refers to the alkyl portion of the moiety and does not describe the number of atoms in the aryl and heteroaryl portion of the moiety.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrarolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

Preferably, heterocycle is selected from 2-azepinone, benzimidazolyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrahydrofuryl, tetrahydroisoquinolinyl, and thienyl.

As appreciated by those of skill in the art, "halo" or "halogen" as used herein is intended to include chloro, fluoro, bromo and iodo.

The alkyl, alkenyl, alkynyl, cycloalkyl, aryl, heteroaryl and heterocyclyl substituents may be substituted or unsubstituted, unless specifically defined otherwise. For example, a ($C_1$-$C_6$) alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: —C=O)CH$_2$CH (OH)CH$_3$, —(C=O)OH, —CH$_2$(OH)CH$_2$CH(O), and so on.

In certain instances, $R^c$ and $R^{c1}$ and $R^f$ and $R^{f1}$ are defined such that they can be taken together with the nitrogen to which they are attached to form a monocyclic or bicyclic heterocycle with 5-7 members in each ring and optionally containing, in addition to the nitrogen, one or two additional heteroatoms selected from N, O and S, said heterocycle optionally substituted with one or more substituents selected from $R^7$. Examples of the heterocycles that can thus be formed include, but are not limited to the following, keeping in mind that the heterocycle is optionally substituted with one or more (and in an embodiment, one, two or three) substituents chosen from $R^7$:

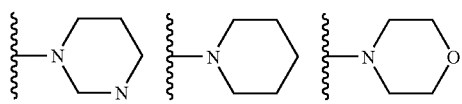

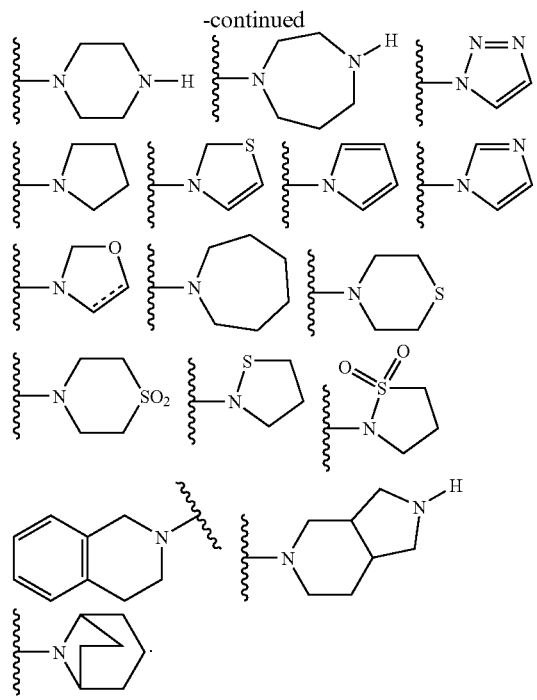

In certain instances, $R^d$ and $R^{d1}$ are defined such that they can be taken together with the phosphorous to which they are attached to form a monocyclic heterocycle with 5-7 members in the ring and optionally containing, in addition to the nitrogen, one or two additional heteroatoms selected from $NR^e$, O and S, said heterocycle optionally substituted with one or more substituents selected from $R^7$. Examples of the heterocycles that can thus be formed include, but are not limited to the following, keeping in mind that the heterocycle is optionally substituted with one or more (and in an embodiment, one or two) substituents chosen from $R^7$:

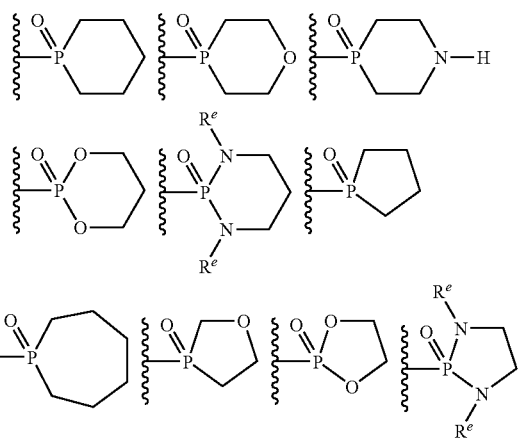

In an embodiment, $R^1$ is selected from H and $C_1$-$C_6$ alkyl.
In an embodiment, $R^2$ is selected from H and $C_1$-$C_6$ alkyl.
In an embodiment, $R^{11}$ and $R^{12}$ are H.
In an embodiment, $R^3$ is selected from —$C_1$-$C_{10}$ alkyl-O—$R^g$ and —$C_1$-$C_{10}$ alkyl-$NR^fR^h$, optionally substituted with one to two substituents selected from $R^{10}$.

In an embodiment, $R^4$ is independently selected from halogen and OH. In a further embodiment, n is 2 and $R^4$ is independently selected from halogen.

In an embodiment, $R^5$ is independently selected from H, halogen and OH.

In an embodiment, t is 1 and $R^{10}$ is fluoro.
In another embodiment, t is 0 and $R^{11}$ is fluoromethyl.
In another embodiment, t is 0 and $R^{12}$ is fluoromethyl.
In an embodiment, $R^{ox}$ is absent.

Included in the instant invention is the free form of compounds of Formula I, as well as the pharmaceutically acceptable salts and stereoisomers thereof. Some of the specific compounds exemplified herein are the protonated salts of amine compounds. The term "free form" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The following abbreviations, used in the Schemes and Examples, are defined below:

| | |
|---|---|
| CDI | 1,1'-carbonyldiimidazole |
| CSP HPLC | Chiral stationary phase high performance liquid chromatography |
| DAST | (diethylamino)sulfur trifluoride |
| DCE | 1,2-dichloroethane |
| DCM | Dichloromethane |
| DMF | Dimethylformamide |
| DMSO | Dimethyl sulfoxide |
| EtOAc | Ethyl acetate |
| LAH | Lithium aluminum hydride |
| LiHMDS | Lithium hexamethyldisilazide |
| MsCl | Methanesulfonylchloride |
| NaHMDS | Sodium hexamethyldisilazide |
| NOE | Nuclear Overhauser Effect |
| PTC | Phase transfer catalyst |
| TBSCl | tert-butyldimethylsilyl chloride |
| TEA | Triethylamine |
| TFA | Trifluoroacetic acid |
| THF | Tetrahydrofuran |

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of Formula I hereinabove.

Schemes

As shown in Scheme A, key 2,2-disubstituted dihydropyrrole intermediate A-8 may be obtained from readily available suitably substituted α-phenylglycines. Following the procedure described by Van Betsbrugge et. al. (*Tetrahedron*, 1997, 53, 9233-9240) the α-allyl-α-phenylglycine is prepared. Reduction of the ester and cyclization with carbonyldiimidazole provides intermediate A-4. Ruthenium oxidation of the allylic olefin, followed by ester formation and alkylation of the nitrogen provides intermediate A-5. Cyclization and decarboxylation results in intermediate A6. The ring carbonyl can then be utilized to incorporate a suitably substituted phenyl moiety. Subsequent saponification and oxygen protection leads to the protected intermediate A-8. The ring nitrogen may then be reacted with triphosgene to provide the activated intermediate A-9.

Scheme B illustrates the preparation of the fluorinated aminopyrrolidine B-4 from the epoxide B-1. Intermediate B-3 is described in Li, Q. et al, *Bioorg. Med. Chenm. Lett.* 8, 1998, 1953-1958. The aminopyrrolidine B4 may then be reacted with intermediate A-9, as illustrated in Scheme C, to provide the bisprotected compound C-1. The acyclic nitrogen may be alkylated as shown. The intermediate C-2 may then be deprotected and ring-nitrogen alkylated to provide the instant compound C-3.

Preparation of the fluorinated aminopyrrolidine D-2 having the cis orientation of the amine and the fluorine starting from the common intermediate B-2 is shown in Scheme D. Preparation of the aminopyrrolidine intermediates having a fluoromethyl moiety in the 5-position (E-5) or the 2-position (F-5) are illustrated in Schemes E and F. These amines may be reacted with intermediate A-9 as illustrated in Scheme C above.

Scheme G illustrates the coupling of the 2-fluoromethyl-3-aminopyrrolidine to intermediate A-9 followed by deprotection and alkylation of the hydroxymethyl moiety on the dihydropyrrole ring.

Scheme H illustrates further elaboration of that hydroymethyl moiety to prepare the instant compounds H-2 and H-3.

The hydroxymethyl moiety may also be oxidized to the corresponding aldehyde I-1 which can then undergo reductive amination to provide the instant compound I-2, as illustrated in Scheme I.

Use of alternative activating group on the amino carbonyl moiety is illustrated in Scheme J.

Scheme K illustrates further homologation of the ring hydroxymethyl moiety. Initially reaction with trimethyl pospohono acetate provides a mixture of the unsaturated alcohol sidechain compound K-1 and the homologous aldehyde K-2. These compounds may be chromatographically separated and utilized to prepare the corresponding amines K-3 and K4.

The aldehyde I-1 may also be reacted with a Grignard reagent to provide the instant compound L-1, as illustrated in Scheme L.

As illustrated in Scheme M, the aldehyde moiety at the 2-position on the dihydropyrrole may also be treated with trimethylphosphonoacetate to provide, after reduction of the conjugated double bond, the ester compound M-2. Lithium aluminum hydride reduction of M-2, followed by Dess-Martin oxidation provide the aldehyde M-4, which can then be reductively aminated as previously described.

Scheme N illustrates fluorination of the C-2 sidechain and subsequent conversion of the hydroxyl moiety to an amine via displacement of the corresponding triflate with sodium azide.

Scheme O illustrates incorporation of a difluoromethyl moiety into the C-2 sidechain.

SCHEME A

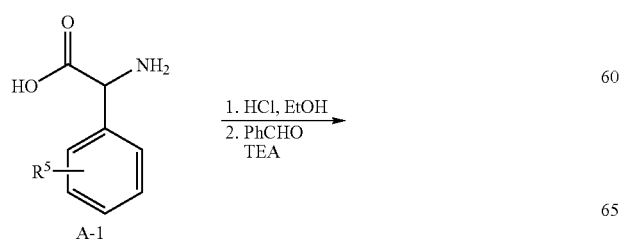

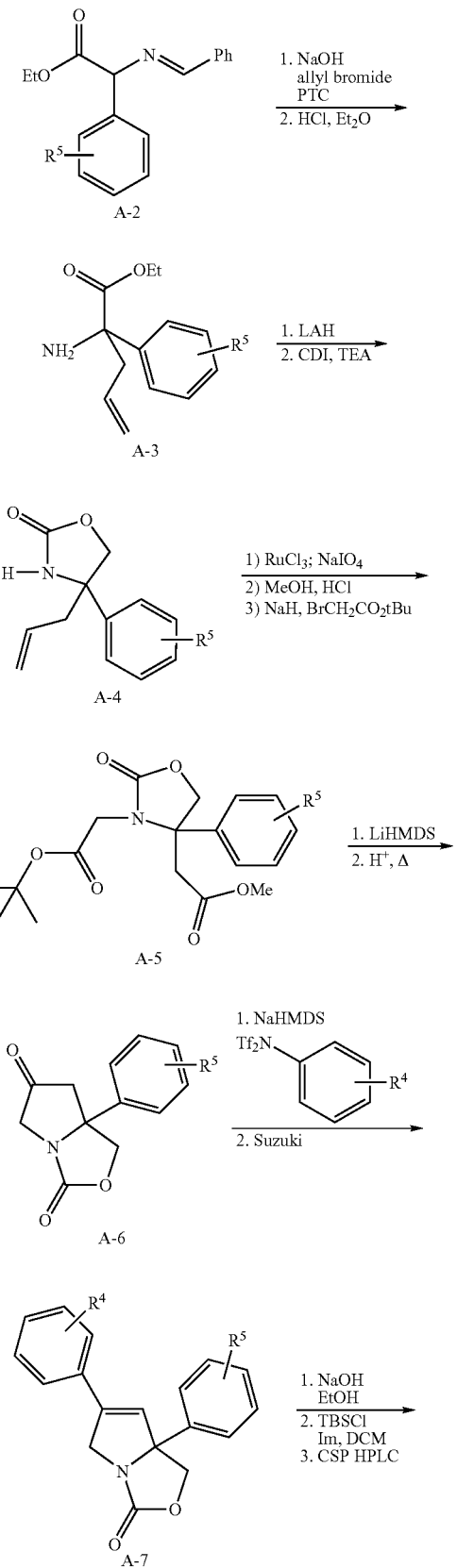

-continued
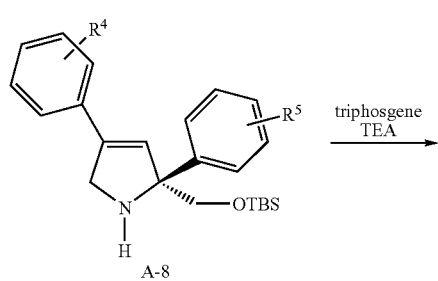
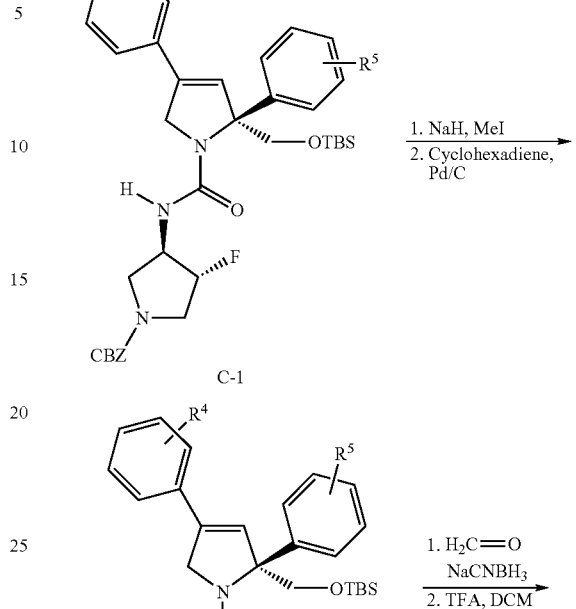
SCHEME B
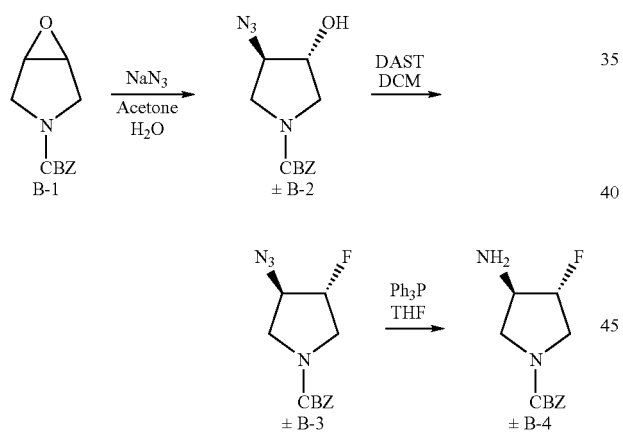
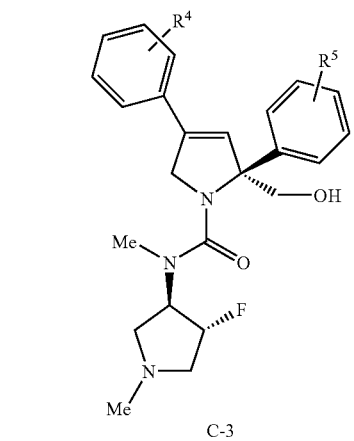
SCHEME C
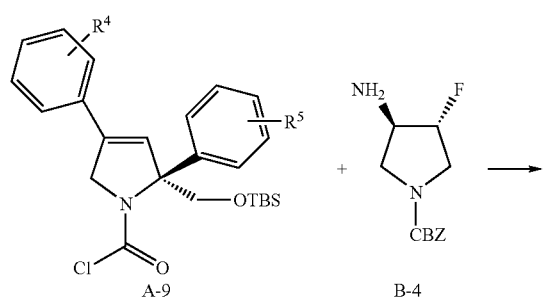
SCHEME D
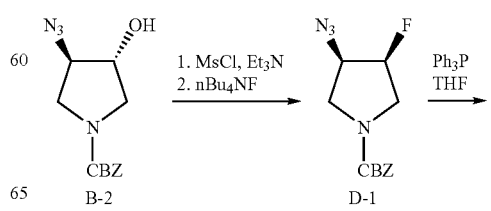

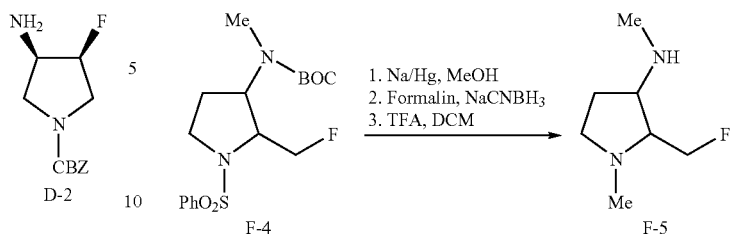
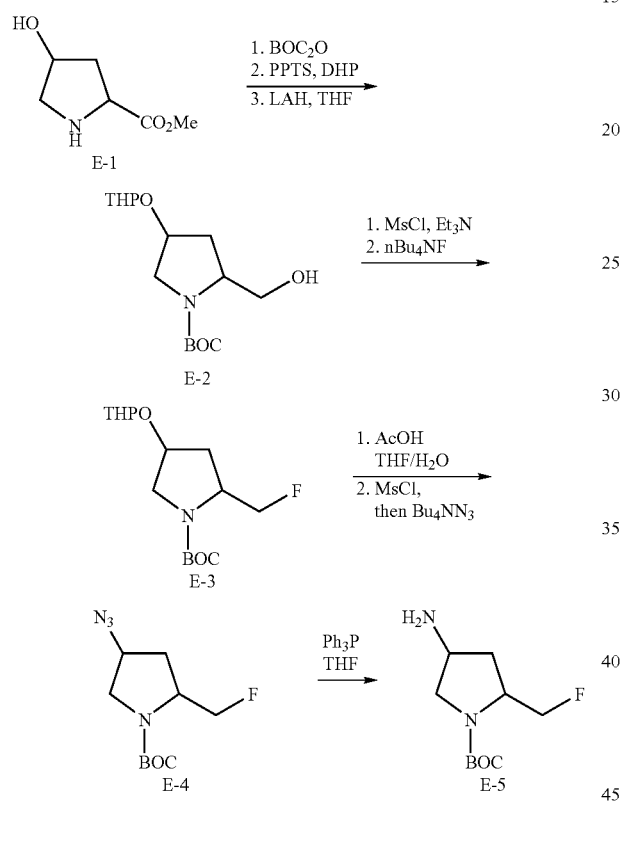
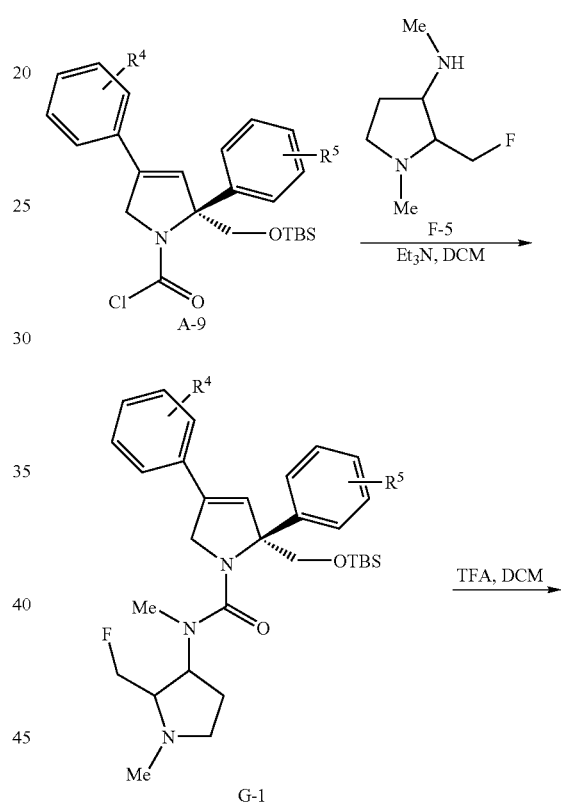
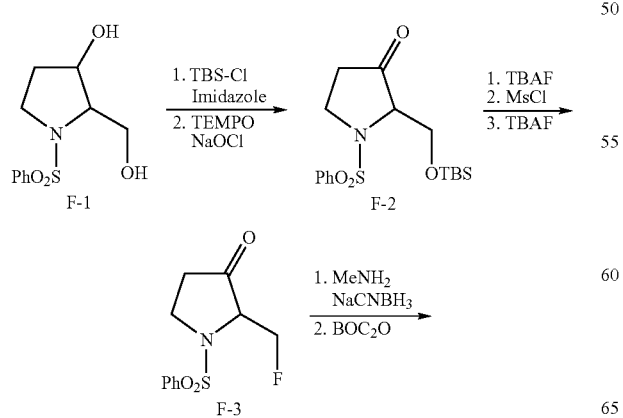
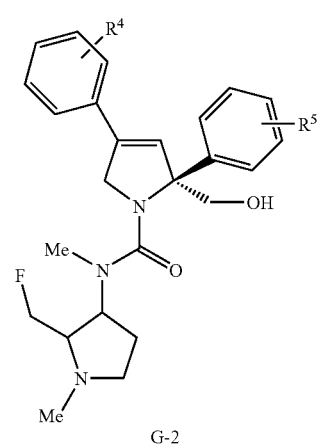

SCHEME H
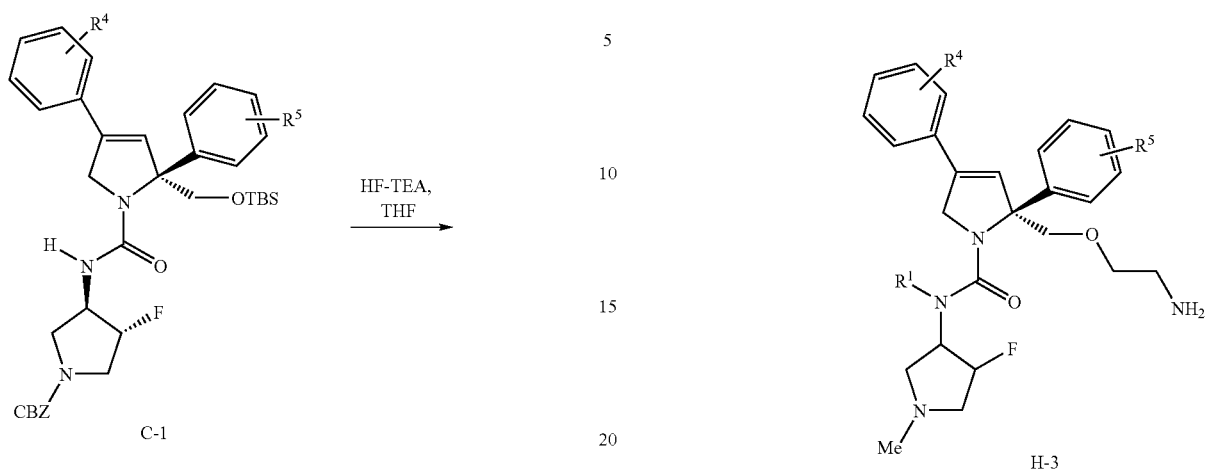
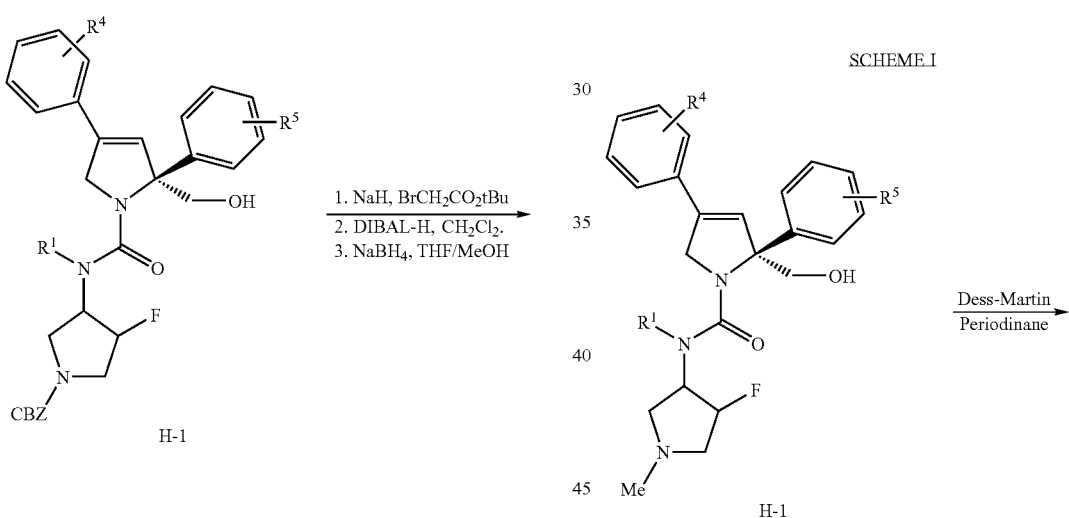
SCHEME I
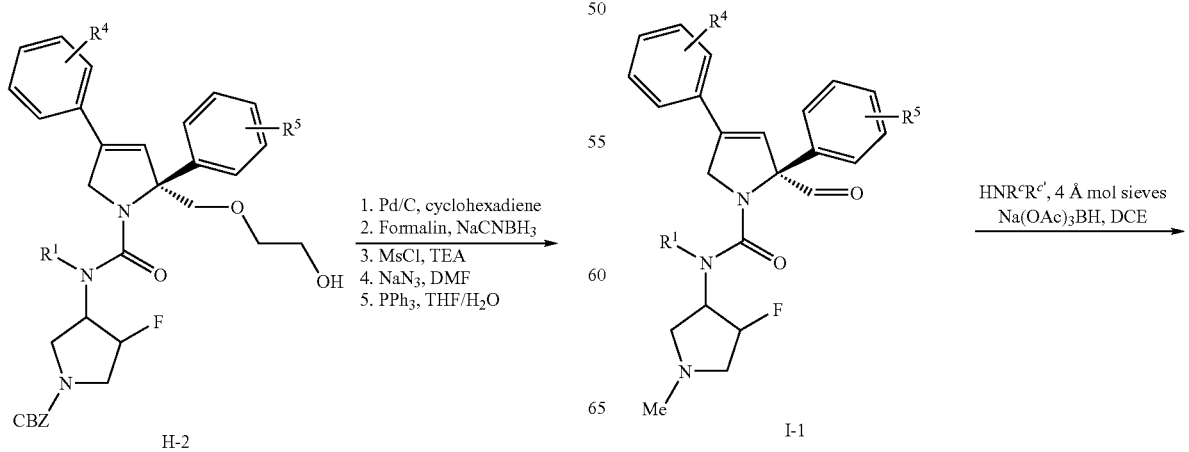

-continued
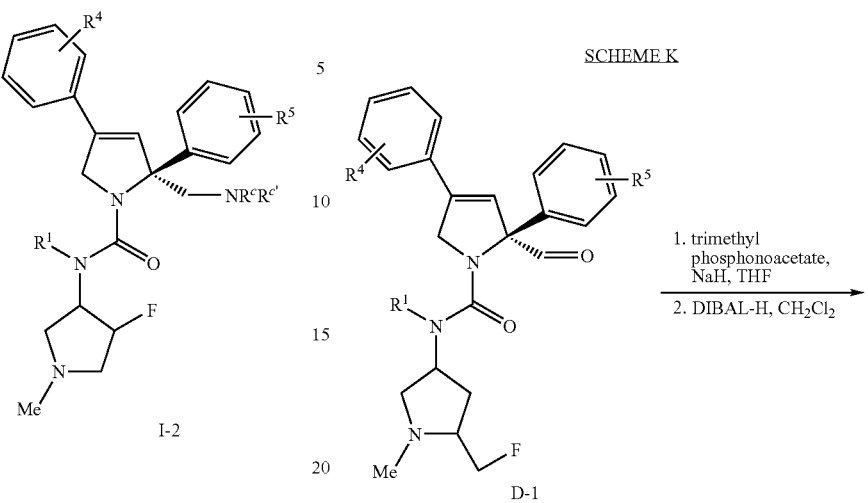
I-2
SCHEME K
SCHEME I
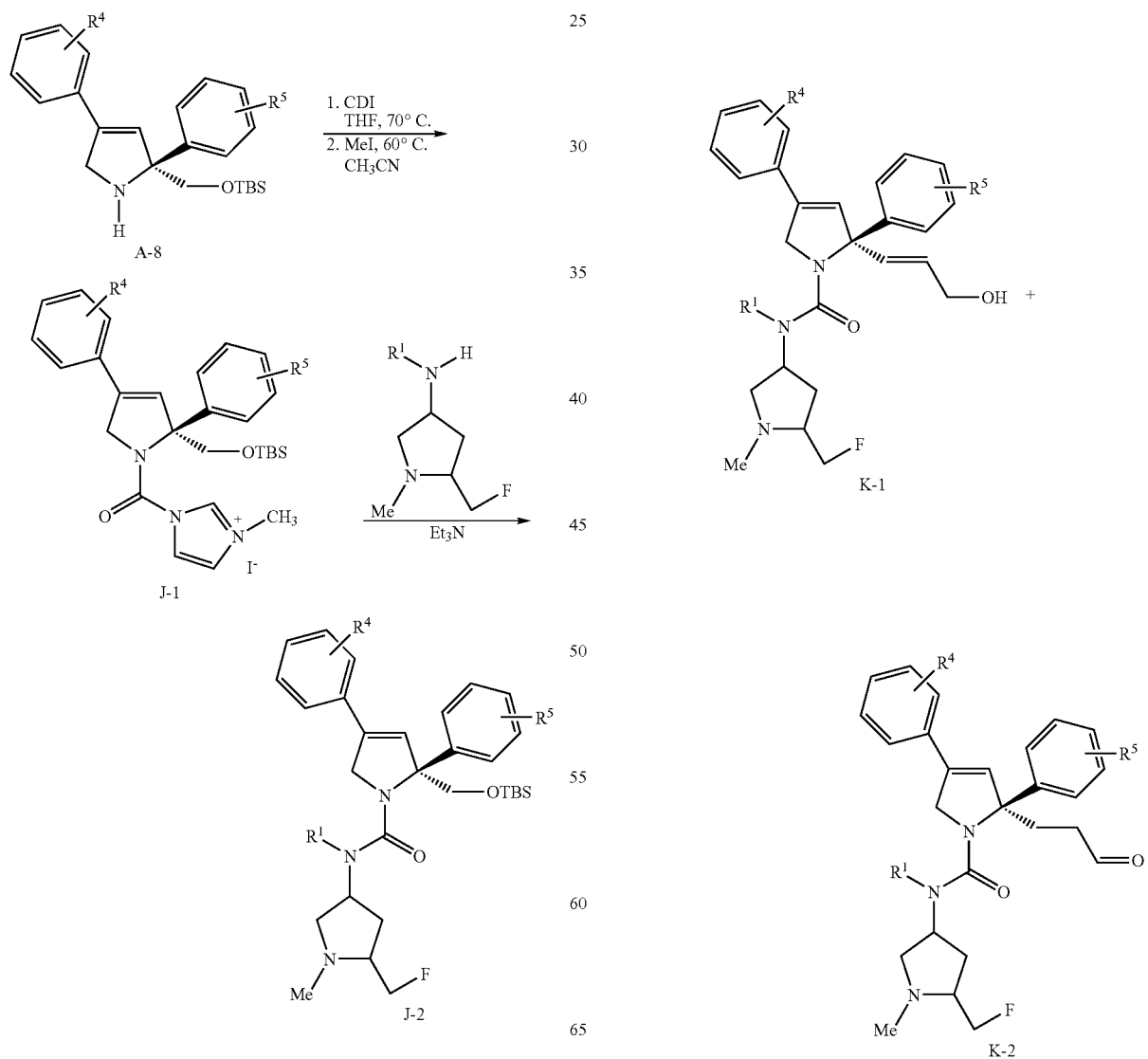

-continued
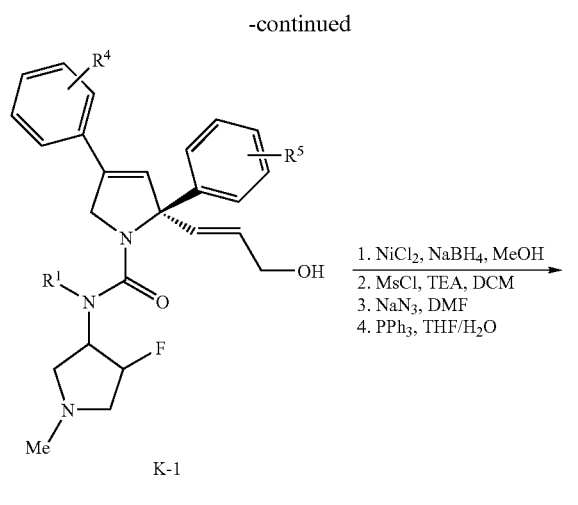
K-1
1. NiCl₂, NaBH₄, MeOH
2. MsCl, TEA, DCM
3. NaN₃, DMF
4. PPh₃, THF/H₂O
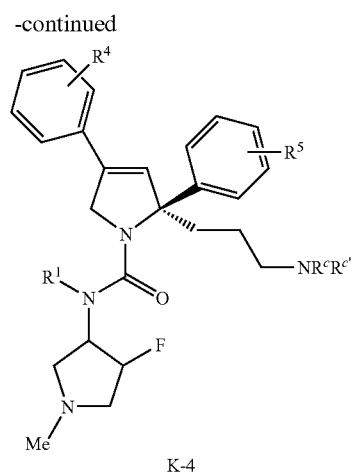
K-4
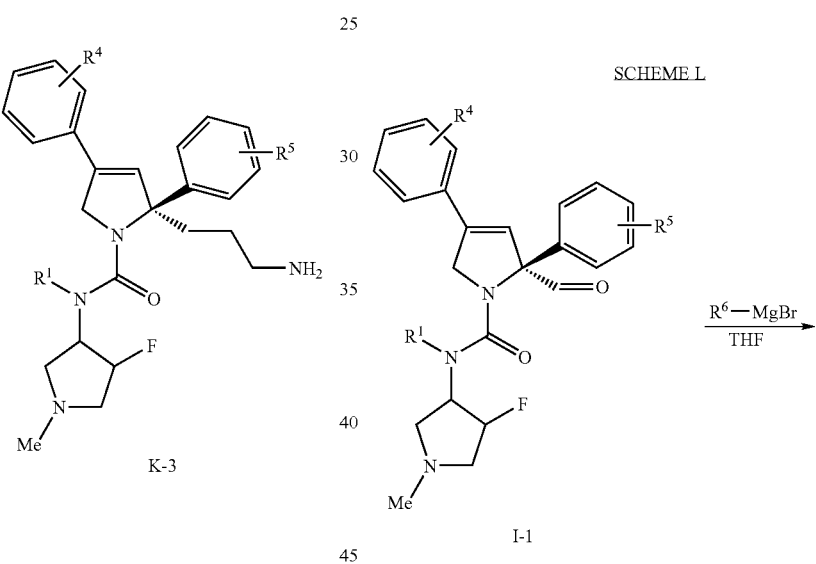
SCHEME L
K-3
I-1
$R^6$—MgBr / THF
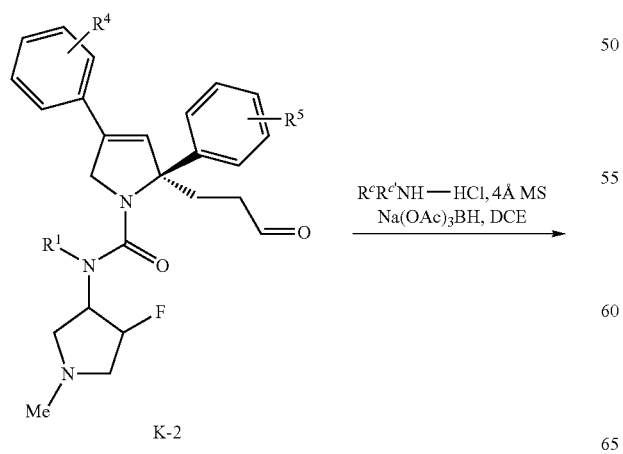
K-2
$R^cR^{c'}NH$—HCl, 4Å MS
Na(OAc)₃BH, DCE
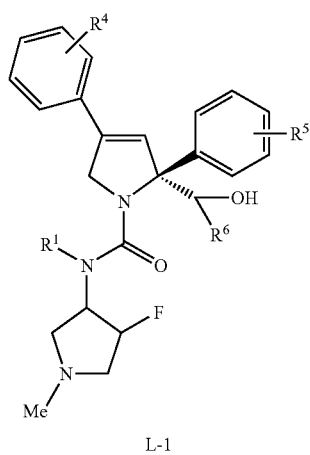
L-1

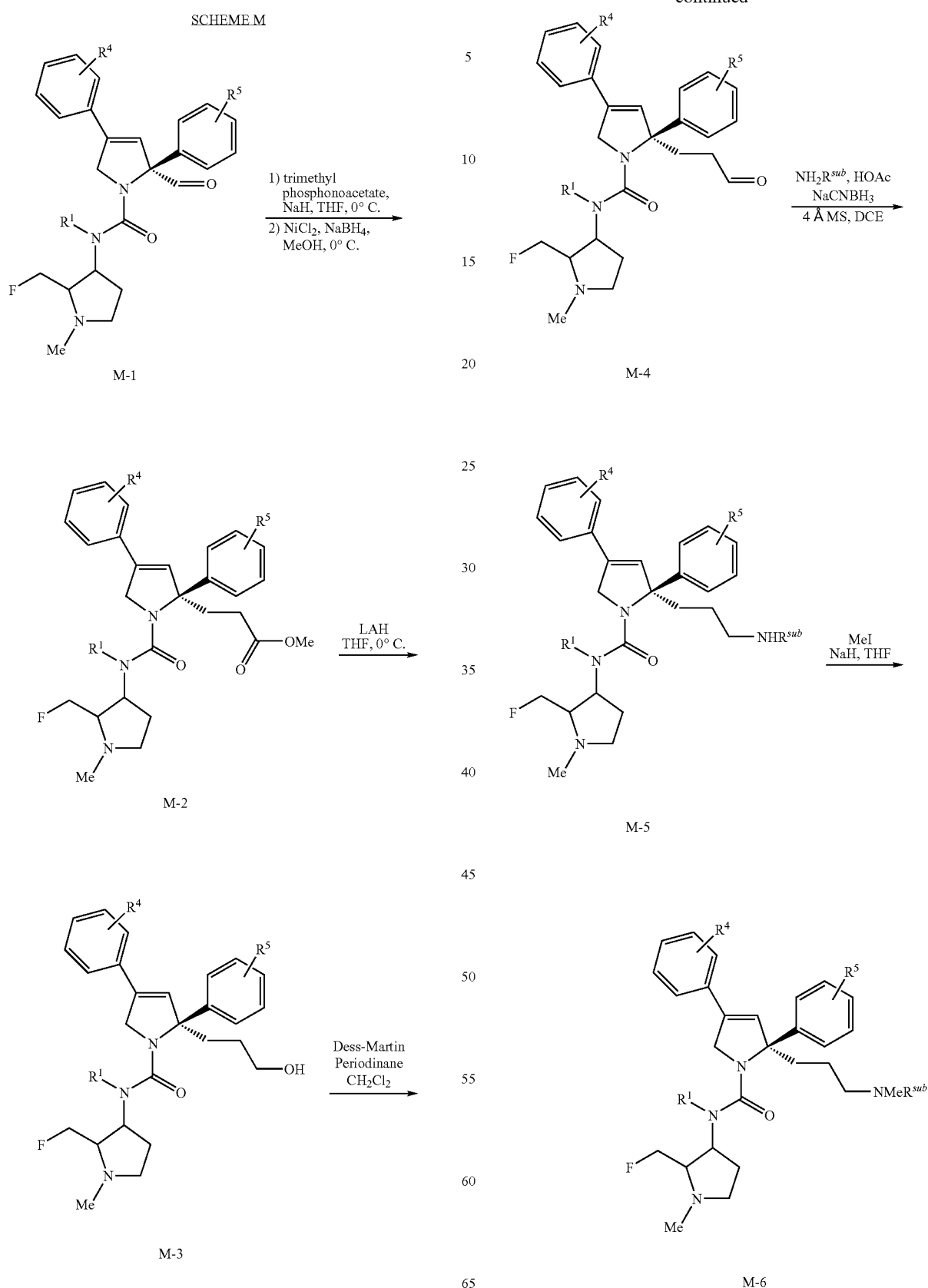

SCHEME N
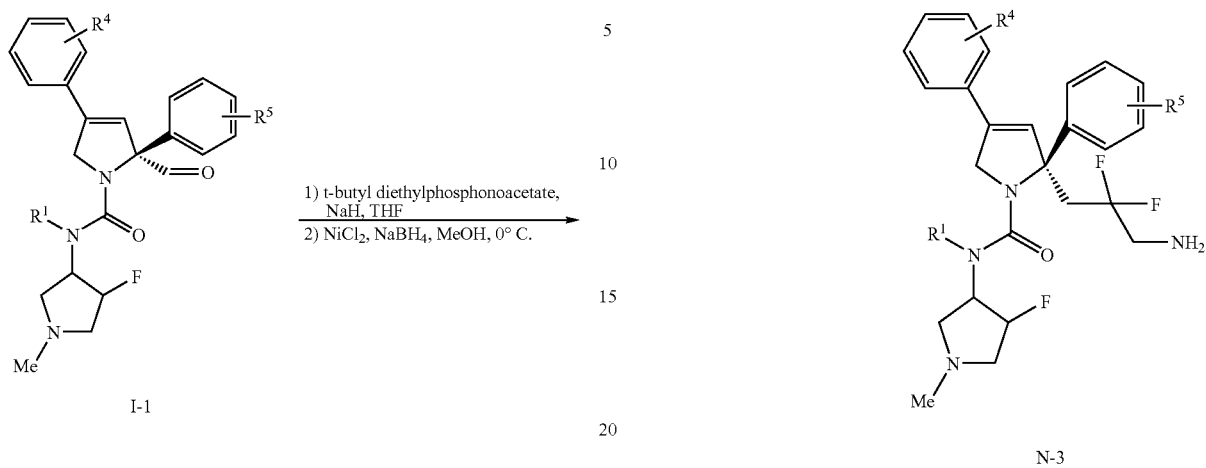
SCHEME O
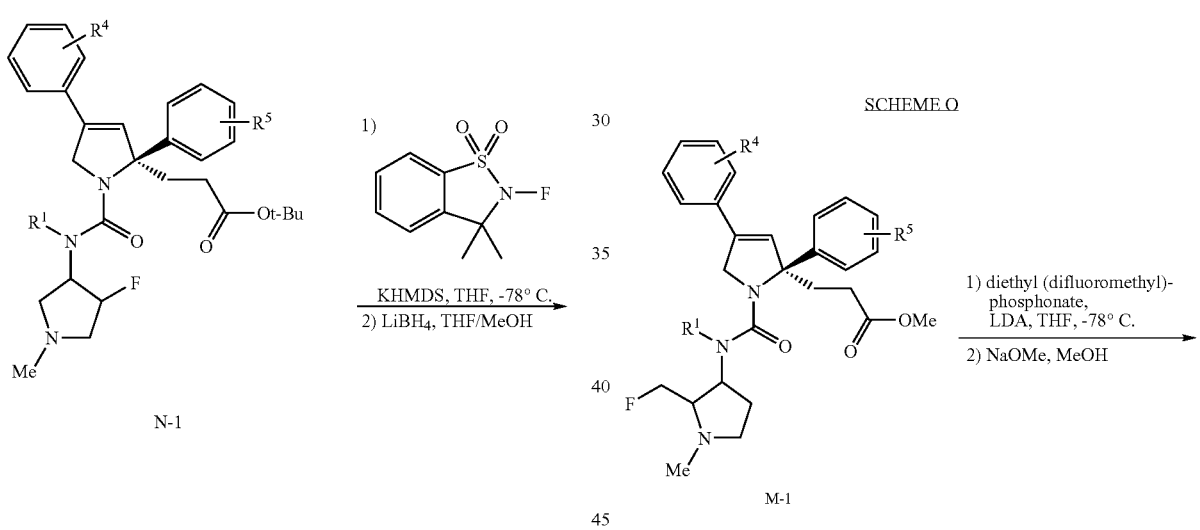
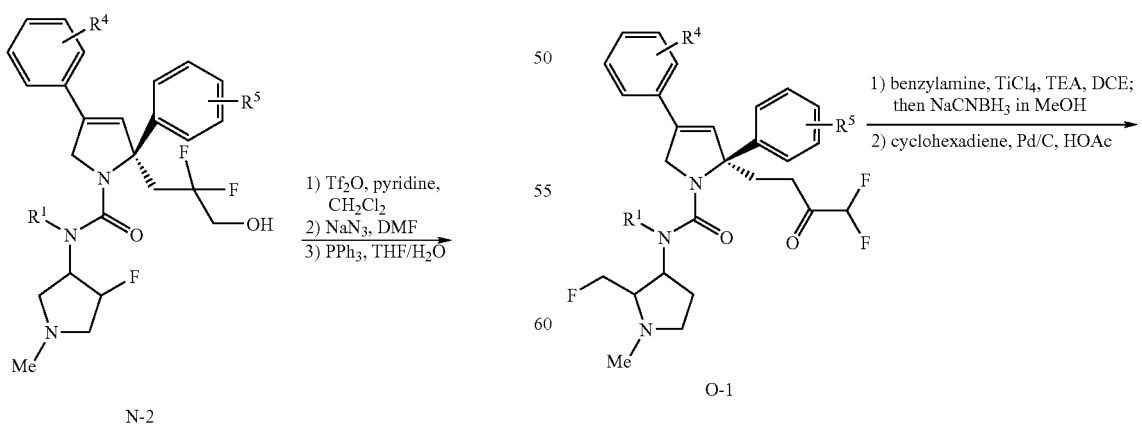

-continued

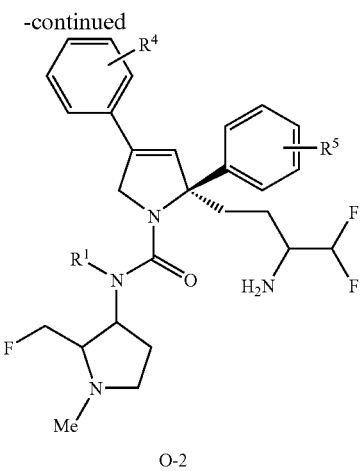

O-2

Utilities

The compounds of the invention find use in a variety of applications. As will be appreciated by those skilled in the art, mitosis may be altered in a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In a preferred embodiment, the compounds of the invention are used to modulate mitotic spindle formation, thus causing prolonged cell cycle arrest in mitosis. By "modulate" herein is meant altering mitotic spindle formation, including increasing and decreasing spindle formation. By "mitotic spindle formation" herein is meant organization of microtubules into bipolar structures by mitotic kinesins. By "mitotic spindle dysfunction" herein is meant mitotic arrest and monopolar spindle formation.

The compounds of the invention are useful to bind to and/or modulate the activity of a mitotic kinesin. In a preferred embodiment, the mitotic kinesin is a member of the bimC subfamily of mitotic kinesins (as described in U.S. Pat. No. 6,284,480, column 5). In a further preferred embodiment, the mitotic kinesin is human KSP, although the activity of mitotic kinesins from other organisms may also be modulated by the compounds of the present invention. In this context, modulate means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. In addition, other mitotic kinesins may be inhibited by the compounds of the present invention.

The compounds of the invention are used to treat cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals afflicted or impending affliction with any one of these disorders or states.

The compounds, compositions and methods provided herein are particularly deemed useful for the treatment of cancer including solid tumors such as skin, breast, brain, cervical carcinomas, testicular carcinomas, etc. More particularly, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematoloric: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

The compounds of the instant invention may also be useful as antifungal agents, by modulating the activity of the fungal members of the bimC kinesin subgroup, as is described in U.S. Pat. No. 6,284,480.

The compounds of the invention are also useful in preparing a medicament that is useful in treating the cellular proliferation diseases described above, in particular cancer.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

As used herein, the term "composition" is intended to encompass a product comprising the specified ingredients in the specific amounts, as well as any product which results, directly or indirectly, from combination of the specific ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycl or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-elrulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl phydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal slin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6<sup>th</sup> edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retioid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide. "Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/rnicrotubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5, 6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino] ethyl]-5-[4-hydroOxy -3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in PCT Publications WO 01/30768 and WO 01/98278, WO 03/050, 064 (Jun. 19, 2003), WO 03/050,122 (Jun. 19, 2003), WO 03/049,527 (Jun. 19, 2003), WO 03/049,679 (Jun. 19, 2003), WO 03/049,678 (Jun. 19, 2003) and WO 03/39460 (May 15, 2003) and pending PCT Appl. Nos. U.S. 03/06403 (filed Mar. 4, 2003), U.S. 03/15861 (filed May 19, 2003), U.S. 03/15810 (filed May 19, 2003), U.S. 03/18482 (filed Jun. 12, 2003) and U. S. 03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro -3H-pyrimidino[5,4-b][1,4]thiazin -6/yl-(S)-ethyl]-2,5-thienoyl-L-glutarnic acid, aminopterin, 5-flurouracil, alanosine, 11-acetyl-8-(carbamoyloxymethyl)-4formyl-6-methoxy-14-oxa-1,11-diazatetracyclo (7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180, 589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry,* pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

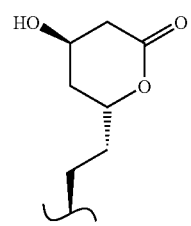

Lactone I

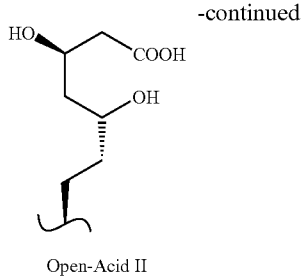

Open-Acid II

In HMG-CoA reductase inhibitors where an open-acid form can exist, salt and ester forms may be formed from the open-acid, and all such forms are included within the meaning of the term "HMG-CoA reductase inhibitor" as used herein. In an embodiment, the HMG-CoA reductase inhibitor is selected from lovastatin and simvastatin, and in a further embodiment, simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-3-chlorophenyl)-1-methyl-2(1H)-quinolinone, (−)-6-[amino(4-chlorophenyl)(1-methyl-1H-imidazol-5-yl)methyl]-4-(3-chlorophenyl)-1-methyl-2(1H)-quinolinone, (+)-6-[amino(4-chlorophenyl)(1-methyl-1H-imidazol-5-yl)methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl)-2-piperazinone, 5(S)-n-Butyl-1-(2-methylphenyl)4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylnimdazol-1-ylmethyl}benzonitrile, 4-{5-[4-hydroxymethyl-4-3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5chloro-2-oxo-2H-[1,2'] bipyridin-5'-ylmethyl]-3H-imidazol-4-ylmethyl}benzonitrile, 4-[3-[4-(2-oxo-2H-[1,2'] bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19 dihydro-19-oxo-5H,17H-6,10:12,16-dimetheno-1H-imidazo[4,3-c][1,11,4] dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacycloeicosine-9-carbonitrile, and (±)-19,20-dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589, 485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359.

For an example of the role of a prenyl-protein transferase inhibitor on angiogenesis see European J. of Cancer, Vol. 35, No. 9, pp.1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI Vol. 69, p. 475 (1982); Arch. Opthalmol., Vol. 108 p.573 (1990); Anat. Rec., Vol. 238, p. 68 (1994); FEBS Letters, Vol. 372, p. 83 (1995); Clin. Orthop.

Vol. 313, p. 76 (1995); J. Mol. Endocrinol., Vol. 16, p.107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A4, squalamine, 6-O-chloroacetylcarbonyl)-fumagillol, thalidornide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp.963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chen La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, $CYC_{202}$ (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 021083064, WO 02/083139, WO 02/083140 and WO 021083138), inhibitors of Raf kinase (for example BAY-43-9006 ), inhibitors of MEK (for example CI-1040 and PD-098059) and inhibitors of mTOR (for example Wyeth CCI-779). Such agents include small molecule inhibitor compounds and antibody antagonists.

"Apoptosis inducing agents" include activators of TNF receptor family members (including the TRAIL receptors).

The combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued November 14, 1995, U.S. Pat. No. 5,633,272, issued May 27, 1997, and U.S. Pat. No. 5,932,598, issued Aug. 3, 1999, all of which are hereby incorporated by reference.

Inhibitors of COX-2 that are particularly useful in the instant method of treatment are:

3-phenyl-4-(4-(methylsulfonyl)phenyl)-2-(5H)-furanone; and

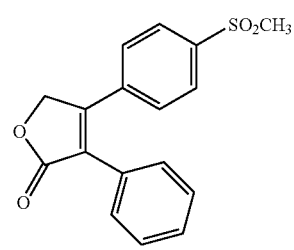

5-chloro-3-(4-methylsulfonyl)phenyl-2-(2-methyl-5-pyridinyl)pyridine;

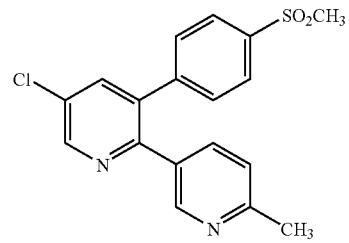

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

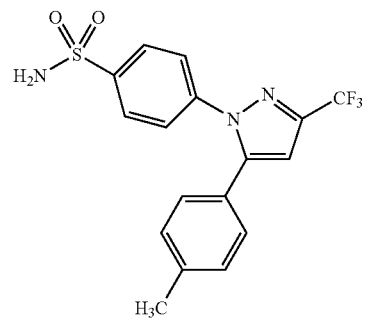

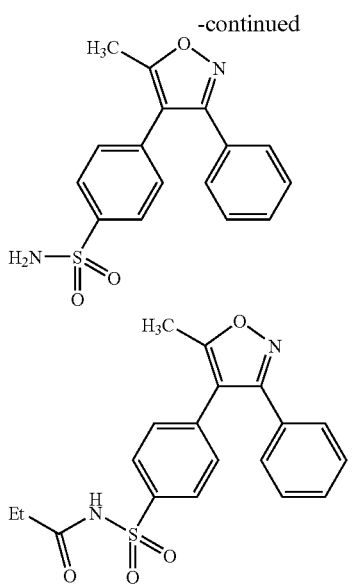

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued November 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostatin, ukrain, ranpirnase, IM862, 5-methoxy4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide,CM101, squalamine, combretastatin, RPI4610, NX31838, sulfated mannopentaose phosphate, 7,7-(carbonyl-bis[imino-N-methyl-4,2-pyrrolocarbonylimino[N-methyl4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-3-ethynylphenyl)-6,7-bis (2-methoxyethoxy)-4-quinazolinanine, BIBX1382, 2,3,9,10, 11,12-hexahydro-10-hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, STI571, CEP2563, 4-(3-chlorophenylamino)-5,6 dimethyl-7H-pyrrolo[2,3-d]pyrimidinemethane sulfonate, 4-(3-bromro4-hydroxyphenyl)amino-6,7-dimethoxyquinazoline, 4-(4'-hydroxyphenyl)amino6,7-dimethoxyquinazoline, SU6668, ST1571A, N-4-chlorophenyl-4-4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999;274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-ipropyl-3-trifluoromethyl-1,2-benzisoxazol-6-yl)oxy]-2-methylpropionic acid (disclosed in U.S. Ser. No. 09/782,856), and 2(R)-7-3-2-chloro-4-fluorophenoxy)phenoxy)propoxy)-2-ethylchromane-2-carboxylic acid (disclosed in U.S. Ser. Nos. 60/235,708 and 60/244, 697).

Another embodiment of the instant invention is the use of the presently disclosed compounds in combination with gene therapy for the treatment of cancer. For an overview of genetic strategies to treating cancer see Hall et al (*Am J Hum Genet* 61:785-789, 1997) and Kufe et al (*Cancer Medicine,* 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy,* August 1998;5(8):1105-13), and interferon gamma (*J Immunol* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokiini-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidoparninergic, such as the phenothiazines (for example prochlorperazine, fluphenaiine, thioridazine and mesoridazine), metoclopramide or dronabinol. For the treatment or prevention of emesis that may result upon administration of the instant compounds, conjunctive therapy with an anti-emesis agent selected from a neurokinin-1 receptor antagonist, a 5HT3 receptor antagonist and a corticosteroid is preferred.

Neuroknin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96121661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-1-(R)-(3,5-bis(triluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anernia. Such an anemia treatment agent is, for example, a continuous eythropoiesis receptor activator (such as epoetin alfa).

A compound of the instant invention may also be administered with an agent useful in the treatment of neutropenia Such a neutropenia treatment agent is, for example, a hematopoietic growth factor which regulates the production and function of neutrophils such as a human granulocyte colony stimulating factor, (G-CSF). Examples of a G-CSF include filgrastiu.

A compound of the instant invention may also be administered with an im-munologic-enhancing drug, such as levarnisole, isoprinosine and Zadaxin.

Thus, the scope of the instant invention encompasses the use of the instantly claimed compounds in combination with a second compound selected from: 1) an estrogen receptor modulator, 2) an androgen receptor modulator, 3) retinoid receptor modulator, 4) a cytotoxic/cytostatic agent, 5) an antiproliferative agent, 6) a prenyl-protein transferase inhibitor, 7) an HMG-CoA reductase inhibitor, 8) an HIV protease inhibitor, 9) a reverse transcriptase inhibitor, 10) an angiogenesis inhibitor, 11) a PPAR-$\gamma$ agonists, 12) a PPAR-$\delta$ agonists, 13) an inhibitor of inherent multidrug resistance, 14) an anti-emetic agent, 15) an agent useful in the treatment of anemia, 16) an agent useful in the treatment of neutropenia, 17) an immunologic-enhancing drug, 18) an inhibitor of cell proliferation and survival signaling, 19) an agent that interfers with a cell cycle checkpoint; and 20) an apoptosis inducing agent.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine linase inhibitor, an inhibitor of epidermal-derived growth factor, an inhibitor of fibroblast-derived growth factor, an inhibitor of platelet derived growth factor, an P (matrix metalloprotease) inhibitor, an integrin blocker, interferon-α interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: 1) an estrogen receptor modulator, 2) an androgen receptor modulator, 3) retinoid receptor modulator, 4) a cytotoxic/cytostatic agent, 5) an antiproliferative agent, 6) a prenyl-protein transferase inhibitor, 7) an HMG-CoA reductase inhibitor, 8) an HIV protease inhibitor, 9) a reverse transcriptase inhibitor, 10) an angiogenesis inhibitor, 11) a PPAR-γ agonists, 12) a PPAR-δ agonists, 13) an inhibitor of inherent multidrug resistance, 14) an anti-emetic agent, 15) an agent useful in the treatment of anemia, 16) an agent useful in the treatment of neutropenia, 17) an immmunologic-enhancing drug, 18) an inhibitor of cell proliferation and survival signaling, 19) an agent that interfers with a cell cycle checkpoint; and 20) an apoptosis inducing agent.

And yet another embodiment of the invention is a method of treating cancer that comprises administering a therapeutically effective amount of a compound of Formula I in combination with paclitaxel or trastuzumab.

The invention ftrther encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: 1) an estrogen receptor modulator, 2) an androgen receptor modulator, 3) a retinoid receptor modulator, 4) a cytotoxic/cytostatic agent, 5) an antiproliferative agent, 6) a prenyl-protein transferase inhibitor, 7) an HMG-CoA reductase inhibitor, 8) an HIV protease inhibitor, 9) a reverse transcriptase inhibitor, 10) an angiogenesis inhibitor, 11) a PPAR-γ agonist, 12) a PPAR-δ agonists; 13) an inhibitor of cell proliferation and survival signaling, 14) an agent that interfers with a cell cycle checkpoint; and an apoptosis inducing agent.

The invention further comprises the use of the instant compounds in a method to screen for other compounds that bind to KSP. To employ the compounds of the invention in a method of screening for compounds that bind to KSP kinesin, the KSP is bound to a support, and a compound of the invention (which is a mitotic agent) is added to the assay. Alternatively, the compound of the invention is bound to the support and KSP is added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the mitotic agent to KSP may be done in a number of ways. In a preferred embodiment, the mitotic agent (the compound of the invention) is labeled, for example, with a fluorescent or radioactive moiety and binding determined directly. For example, this may be done by attaching all or a portion of KSP to a solid support, adding a labeled mitotic agent (for example a compound of the invention in which at least one atom has been replaced by a detectable isotope), washing off excess reagent, and determining whether the amount of the label is that present on the solid support Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific-binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}$I, or with fluorophores. Alternatively, more than one component may be labeled with different labels; using $^{125}$I for the proteins, for example, and a fluorophor for the mitotic agents.

The compounds of the invention may also be used as competitors to screen for additional drug candidates. "Candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, preferred embodiments exclude molecules already known to bind to that particular protein, for example, polymer structures such as microtubules, and energy sources such as ATP. Preferred embodiments of assays herein include candidate agents which do not bind the cellular proliferation protein in its endogenous native state termed herein as "exogenous" agents. In another preferred embodiment, exogenous agents further exclude antibodies to KSP.

Candidate agents can encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Competitive screening assays may be done by combining KSP and a drug candidate in a first sample. A second sample comprises a mitotic agent, KSP and a drug candidate. This may be performed in either the presence or absence of microtubules. The binding of the drug candidate is determined for both samples, and a change, or difference in binding between the two samples indicates the presence of an agent capable of binding to KSP and potentially modulating its activity. That is, if the binding of the drug candidate is different in the second sample relative to the first sample, the drug candidate is capable of binding to KSP.

In a preferred embodiment, the binding of the candidate agent is determined through the use of competitive binding assays. In this embodiment, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In one embodiment, the candidate agent is labeled. Either the candidate agent, or the competitor, or both, is added first to KSP for a time sufficient to allow binding, if present Incubations may be performed at any temperature which facilitates optimal activity, typically between about 4 and about 40° C.

Incubation periods are selected for optimum activity, but may also be optimized to facilitate rapid high throughput screening. Typically between 0.1 and 1 hour will be sufficient Excess reagent is generally removed or washed away. The second component is then added, and the presence or absence of the labeled component is followed, to indicate binding.

In a preferred embodiment, the competitor is added first, followed by the candidate agent. Displacement of the competitor is an indication the candidate agent is binding to KSP and thus is capable of binding to, and potentially modulating, the activity of KSP. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to KSP with a higher affinity. Thus, if the candidate agent is labeled, the presence of the label on the support, coupled with a lack of competitor binding, may indicate the candidate agent is capable of binding to KSP.

It may be of value to identify the binding site of KSP. This can be done in a variety of ways. In one embodiment, once KSP has been identified as binding to the mitotic agent, KSP is fragmented or modified and the assays repeated to identify the necessary components for binding.

Modulation is tested by screening for candidate agents capable of modulating the activity of KSP comprising the steps of combining a candidate agent with KSP, as above, and determining an alteration in the biological activity of KSP. Thus, in this embodiment, the candidate agent should both bind to KSP (although this may not be necessary), and alter its biological or biochemical activity as defined herein. The methods include both in vitro screening methods and in vivo screening of cells for alterations in cell cycle distribution, cell viability, or for the presence, morphology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

These and other aspects of the invention will be apparent from the teachings contained herein.

Assays

The compounds of the instant invention described in the Examples were tested by the assays described below and were found to have kinase inhibitory activity. Other assays are known in the literature and could be readily performed by those of skill in the art (see, for example, PCT Publication WO 01/30768, May 3, 2001, pages 18-22).

I. Kinesin ATPase In Vitro Assay

Cloning and Expression of Human Poly-Histidine Tagged KSP Motor Domain (KSP(367H))

Plasmids for the expression of the human KSP motor domain construct were cloned by PCR using a pBluescript full length human KSP construct (Blangy et al., Cell, vol.83, pp1159-1169, 1995) as a template. The N-terminal primer 5'-GCAACGATTAATATGGCGTCGCAGC-CAAATTCGTCTGCGAAG (SEQ.ID.NO.: 1) and the C-terminal primer 5'-GCAACGCRCGAGTCAGTGAT GATG-GTGGTGATGCTGATTCACTTCAGGCTTATTCAATAT (SEQ.ID.NO.: 2) were used to amplify the motor domain and the neck linker region. The PCR products were digested with AseI and XhoI, ligated into the NdeIIXhoI digestion product of pRSETa (Invitrogen) and transformed into E. coli BL21 (DE3).

Cells were grown at 37° C. to an $OD_{600}$ of 0.5. After cooling the culture to room temperature expression of KSP was induced with 100 μM IPTG and incubation was continued overnight Cells were pelleted by centrifugation and washed once with ice-cold PBS. Pellets were flash-frozen and stored −80° C.

Protein Purification

Cell pellets were thawed on ice and resuspended in lysis buffer (50 mM K-HEPES, pH 8.0, 250 mM KCl, 0.1% Tween, 10 mM imidazole, 0.5 mM Mg-ATP, 1 mM PMSF, 2 mM benzimidine, 1× complete protease inhibitor cocktail (Roche)). Cell suspensions were incubated with 1 mg/ml lysozyme and 5 mM β-mercaptoethanol on ice for 10 minutes, followed by sonication (3×30 sec). All subsequent procedures were performed at 4° C. Lysates were centrifuged at 40,000×g for 40 minutes. Supernatants were diluted and loaded onto an SP Sepharose column (Pharmacia, 5 ml cartridge) in buffer A (50 mM K-HEPES, pH 6.8, 1 mM $MgCl_2$, 1 mM EGTA, 10 μM Mg-ATP, 1 mM DTT) and eluted with a 0 to 750 mM KCl gradient in buffer A. Fractions containing KSP were pooled and incubated with Ni—NTA resin (Qiagen) for one hour. The resin was washed three times with buffer B (Lysis buffer minus PMSF and protease inhibitor cocktail), followed by three 15-minute incubations and washes with buffer B. Finally, the resin was incubated and washed for 15 minutes three times with buffer C (same as buffer B except for pH 6.0) and poured into a column. KSP was eluted with elution buffer (identical to buffer B except for 150 mM KCl and 250 mM imidazole). KSP-containing fractions were pooled, made 10% in sucrose, and stored at −80° C.

Microtubules are prepared from tubulin isolated from bovine brain. Purified tubulin (>97% MAP-free) at 1 mg/ml is polymerized at 37° C. in the presence of 10 μM paclitaxel, 1 mM DTT, 1 mM GTP in BRB80 buffer (80 mM K-PIPES, 1 mM EGTA, 1 mM $MgCl_2$ at pH 6.8). The resulting microtubules are separated from non-polymerized tubulin by ultracentrifugation and removal of the supernatant. The pellet, containing the microtubules, is gently resuspended in 10 μM paclitaxel, 1 mM DTT, 50 μg/ml ampicillin, and 5 μg/ml chloramphenicol in BRB80.

The kinesin motor domain is incubated with microtubules, 1 MM ATP (1:1 $MgCl_2$: Na-ATP), and compound at 23° C. in buffer containing 80 mM K-HEPES (pH 7.0), 1 mM EGTA, 1 mM DTT, 1 mM $MgCl_2$, and 50 mM KCl. The reaction is terminated by a 2-10 fold dilution with a final buffer composition of 80 mM HEPES and 50 mM EDTA. Free phosphate from the ATP hydrolysis reaction is measured via a quinaldine red/ammonium molybdate assay by adding 150 μl of quench C buffer containing a 2:1 ratio of quench A:quench B. Quench A contains 0.1 mg/ml quinaldine red and 0.14% polyvinyl alcohol; quench B contains 12.3 mM ammonium molybdate tetrahydrate in 1.15 M sulfuric acid. The reaction is incubated for 10 minutes at 23° C., and the absorbance of the phosphomolybdate complex is measured at 540 nm.

The compounds of the instant invention may be tested in the above assay and an $IC_{50}$ found.

II. Cell Proliferation Assay

Cells are plated in 96-well tissue culture dishes at densities that allow for logarithmic growth over the course of 24, 48, and 72 hours and allowed to adhere overnight. The following day, compounds are added in a 10-point, one-half log titration to all plates. Each titration series is performed in triplicate, and a constant DMSO concentration of 0.1% is maintained throughout the assay. Controls of 0.1% DMSO alone are also included. Each compound dilution series is made in media without serm The final concentration of serum in the assay is 5% in a 200 μL volume of media Twenty microliters of Alamar blue staining reagent is added to each sample and control well on the titration plate at 24, 48, or 72 hours following the addition of drug and returned to incubation at 37° C. Alamar blue fluorescence is analyzed 6-12 hours later on a CytoFluor II plate reader using 530-560 nanometer wavelength excitation, 590 nanometer emission.

A cytotoxic $EC_{50}$ is derived by plotting compound concentration on the x-axis and average percent inhibition of cell growth for each titration point on the y-axis. Growth of cells in control wells that have been treated with vehicle alone is defined as 100% growth for the assay, and the growth of cells treated with compounds is compared to this value. Proprietary in-house software is used to calculate percent cytotoxicity values and inflection points using logistic 4-parameter curve fitting. Percent cytotoxicity is defined as:

% cytotoxicity:(Fluorescence$_{control}$)−(Flourescence$_{sample}$)×100 × (Flourescence$_{control}$)$^{-1}$ The inflection point is reported as the cytotoxic $EC_{50}$.

III. Evaluation of Mitotic Arrest and Apoptosis by FACS

FACS analysis is used to evaluate the ability of a compound to arrest cells in mitosis and to induce apoptosis by measuring DNA content in a treated population of cells. Cells are seeded at a density of 1.4×10$^6$ cells per 6 cm$^2$ tissue culture dish and allowed to adhere overnight. Cells are then treated with vehicle (0.1% DMSO) or a titration series of compound for 8-16 hours. Following treatment, cells are harvested by trypsinization at the indicated times and pelleted by centrifugation. Cell pellets are rinsed in PBS and fixed in 70% ethanol and stored at 4° C. overnight or longer.

For FACS analysis, at least 500,000 fixed cells are pelleted and the 70% ethanol is removed by aspiration. Cells are then incubated for 30 min at 4° C. with RNase A (50 Kunitz units/ml) and propidium iodide (50 μg/ml), and analyzed using a Becton Dickinson FACSCaliber. Data (from 10,000 cells) is analyzed using the Modfit cell cycle analysis modeling software (Verity Inc.).

An $EC_{50}$ for mitotic arrest is derived by plotting compound concentration on the x-axis and percentage of cells in the G2/M phase of the cell cycle for each titration point (as measured by propidium iodide fluorescence) on the y-axis. Data analysis is performed using the SigmaPlot program to calculate an inflection point using logistic 4-parameter curve fitting. The inflection point is reported as the $EC_{50}$ for mitotic arrest. A similar method is used to determine the compound $EC_{50}$ for apoptosis. Here, the percentage of apoptotic cells at each titration point (as determined by propidium iodide fluorescence) is plotted on the y-axis, and a similar analysis is carried out as described above.

IV. Immunofluorescence Microscopy to Detect Monopolar Spindles

Methods for immunofluorescence staining of DNA, tubulin, and pericentrin are essentially as described in Kapoor et al. (2000) J. Cell Biol. 150: 975-988. For cell culture studies, cells are plated on tissue culture treated glass chamber slides and allowed to adhere overnight. Cells are then incubated with the compound of interest for 4 to 16 hours. After incubation is complete, media and drug are aspirated and the chamber and gasket are removed from the glass slide. Cells are then permeabiued, fixed, washed, and blocked for non-specific antibody binding according to the referenced protocol. Paraffin-enbedded tumor sections are deparaffinized with xylene and rehydrated through an ethanol series prior to blocking. Slides are incubated in primary antibodies (mouse monoclonal anti-α-tubulin antibody, clone DM1A from Sigma diluted 1:500; rabbit polyclonal anti-pericentrin antibody from Covance, diluted 1:2000) overnight at 4° C. After washing, slides are incubated with conjugated secondary antibodies (FTC-conjugated donkey anti-mouse IgG for tubulin; Texas red-conjugated donkey anti-rabbit IgG for pericentrin) diluted to 15 μg/ml for one hour at room temperature. Slides are then washed and counterstained with Hoechst 33342 to visualize DNA. Immunostained samples are imaged with a 100x oil immersion objective on a Nikon epifluorescence microscope using Metamorph deconvolution and imaging software.

EXAMPLES

Examples provided are intended to assist in a further understanding of the invention. Particular materials employed, species and conditions are intended to be illustrative of the invention and not limiting of the reasonable scope thereof.

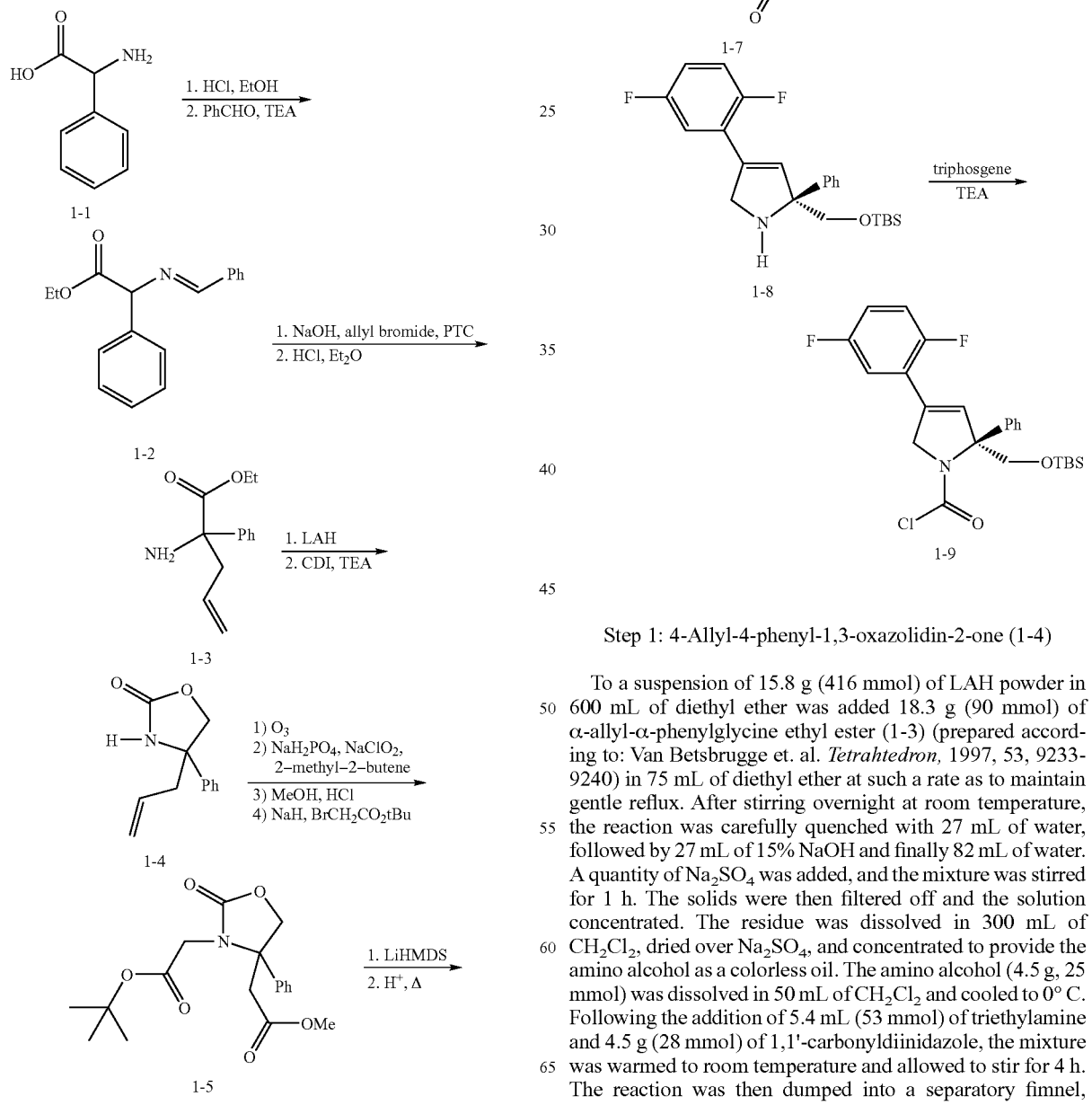

Step 1: 4-Allyl-4-phenyl-1,3-oxazolidin-2-one (1-4)

To a suspension of 15.8 g (416 mmol) of LAH powder in 600 mL of diethyl ether was added 18.3 g (90 mmol) of α-allyl-α-phenylglycine ethyl ester (1-3) (prepared according to: Van Betsbrugge et. al. *Tetrahtedron*, 1997, 53, 9233-9240) in 75 mL of diethyl ether at such a rate as to maintain gentle reflux. After stirring overnight at room temperature, the reaction was carefully quenched with 27 mL of water, followed by 27 mL of 15% NaOH and finally 82 mL of water. A quantity of $Na_2SO_4$ was added, and the mixture was stirred for 1 h. The solids were then filtered off and the solution concentrated. The residue was dissolved in 300 mL of $CH_2Cl_2$, dried over $Na_2SO_4$, and concentrated to provide the amino alcohol as a colorless oil. The amino alcohol (4.5 g, 25 mmol) was dissolved in 50 mL of $CH_2Cl_2$ and cooled to 0° C. Following the addition of 5.4 mL (53 mmol) of triethylamine and 4.5 g (28 mmol) of 1,1'-carbonyldiimidazole, the mixture was warmed to room temperature and allowed to stir for 4 h. The reaction was then dumped into a separatory finnel, washed twice with 1M HCl, water, dried over $Na_2SO_4$, and concentrated to obtain oxazolidinone 1-4 as a colorless oil. Data for 1-4: 1HNMR (500 MHz, CDCl$_3$) δ 7.4 -7.2 (m, 5H), 6.6 (s, 1H), 5.6 -5.5 (m, 1H), 5.2 (m, 2H), 4.5 (d, 1H), 4.35 (d, 1H), 2.8 (m, 1H), 2.6 (m, 1H) ppm.

Step 2: Diester (1-5)

A solution of 68 g (334.6 mmol) of 1-4 in 500 mL of CH$_2$Cl$_2$ was cooled to –78° C. and ozone was bubbled through the solution until a pale blue color persisted. O$_2$ was then bubbled through the solution for 15 minutes, followed by 30 minutes with N$_2$. At that time, 491 mL (6.7 moles) of dimethyl sulfide was added, and the solution was stirred overnight while slowly coming to room temperature. The volitiles were removed by rotary evaporation to provide a brown oil. This material was suspended in 1L of tBuOH, and 200 mL (1.9 moles) of 2-methyl-2-butene was added. To this solution was then added dropwise a mixture of 160 g (1.33 moles) of NaH$_2$PO$_4$ and 70 g (774 mmol) of NaClO$_2$ in 800 mL of H$_2$O. After the addition was complete, the mixture was stirred for an additional 4 h. After separating the layers, the organic was concentrated by rotary evaporation, the residue was dissolved in EtOAc and placed in a separatory funnel with the aqueous phase from the reaction. After separation, the aqueous phase was extracted 3× with EtOAc, dried over Na$_2$SO$_4$, and concentrated to provide ~90 g of a yellow gum. This residue was suspended in 500 mL of MeOH, and HCl gas was bubbled through the solution until it was nearly refluxing. The flask was then capped and allowed to stir overnight while cooling to room temperature. The volitiles were removed by rotary evaporation, the residue was loaded onto a silica gel column in CH$_2$Cl$_2$, and eluted with EtOAc/hexanes to provide the methyl ester as a pale orange gum. This residue was dissolved in 500 mL of THF, cooled to 0° C., and 32.6 mL (220.5 mmol) of tert-butyl bromoacetate was added, followed by 10.6 g of NaH (264.6 mmol of a 60% suspension). After the mixture was allowed to warm to room temperature and stir overnight, it was quenched with a saturated NH$_4$Cl solution, and extracted twice with EtOAc. The combined organic layers were then washed with brine, dried over Na$_2$SO$_4$, concentrated, and the residue purified by silica gel chromatography with EtOAc/hexanes to provide 1-5 as a thick pale yellow gum. Data for 1-5: $^1$HNMR (500 MHz, CDCl$_3$) δ 7.4 -7.3 (m, 5H), 4.65 (d, 1H), 4.55 (d, 1H), 3.9 (d, 1H), 3.65 (s, 1H), 3.5 (d, 1H), 3.35 (d, 1H), 3.2 (d, 1H), 1.4 (s, 9H) ppm. HRMS (ES) calc'd M+Na for C$_{18}$H$_{23}$NO$_6$: 372.1423. Found: 372.1412.

Step 3: 7a-Phenyldihydro-1H-pyrrolo[1,2-c][1,3]oxazole-3,6(5H)-dione (1-6)

To a solution of 18.6 g (53 mmol) of 1-5 in 150 mL of TBF at –78° C. was added dropwise 58.6 mL (58.6 mmol) of a 1M solution of LiHMDS in THF. After stirring for 1 h at that temperature, the cooling bath was removed and the reaction was allowed to warm to room temperature and stir overnight. The mixture was quenched with a saturated NH$_4$Cl solution, extracted twice with EtOAc, washed twice with brine, dried over Na$_2$SO$_4$ and concentrated. The residue was dissolved in 60 mL of formic acid and heated at 100° C. for 24 h. The volatiles were removed under vacuum and the residue was triturated with CH$_2$Cl$_2$/hexanes/Et$_2$O to provide 1-6 as a beige solid. Data for 1-6: $^1$HNMR (500 MHz, CDCl$_3$) δ 7.5-7.3 (m, 5H), 4.7 (d, 1H), 4.3 (d, 1H), 4.2 (d, 1H), 3.5 (d, 1H), 3.1 (d, 1H), 2.95 (d, 1H), 2.9 (d, 1H) ppm.

Step 4: 6-(2.5-Difluorophenyl)-7a-phenyl-5,7a-dihydro-1H-pyrrolo[1,2-c][1,3]oxazol-3-one (1-7)

To a suspension of 2.2 g (10 mmol) of 1-7 in 150 mL of THF at –78° C. was added dropwise 12.2 mL (12.2 mmol) of a 1M solution of NaHMDS in THF. After stirring for 30 min, the solution was allowed to warm to 0° C. and held there for 1 h. The solution was then cooled back down to –78° C. and a solution of 4.35 g (12.2 mmol) of N-phenylbis(trifluoromethanesulphonimide) in 10 mL of THF was added. The cooling bath was removed and the mixture was allowed to warm to room temperature and stir overnight. The mixture was quenched with a saturated NH$_4$Cl solution, extracted twice with EtOAc, washed twice with brine, dried over Na$_2$SO$_4$ and concentrated. The residue was dissolved in 75 mL of DME and 18 mL of water. To this mixture was added 1.29g (30 mmol) of LiCl, 3.2 g (30 mmol) of Na$_2$CO$_3$, and 4.8 g (30 mmol) of 2,5-difluorophenylboronic acid. The solution was then degassed with N$_2$ for 1 minute, followed by the addition of 630 mg (0.5 mmol) of tetrakis(triphenylphosphine)palladium (0). The reaction was heated at 90° C. for 3 h, cooled to room temperature, diluted with saturated NaHCO$_3$, and extracted twice with EtOAc. The combined organic layers were washed with brine, dried over Na$_2$SO$_4$, concentrated, and the residue purified by silica gel chromatography with CH$_2$Cl$_2$/hexanes to provide 1-7 as a white solid. Data for 1-7: $^1$HNMR (500 MHz, CDCl$_3$) δ 7.5-7.3 (m, 5H), 7.1-6.9 (m, 3H), 6.8 (s, 1H), 4.9 (d, 1H), 4.75 (d, 1H), 4.5 (d, 1H), 4.23 (d, 1H) ppm. HRMS (ES) calc'd M+H for C$_{18}$H$_{13}$F$_2$NO$_2$: 314.0987. Found: 314.0993.

Step 5: 2-({[tert-Butyl(dimethyl)silyl]oxy}methyl)-4-(2,5-difluorophenyl)-2-phenyl-2,5-dihydro-1H-pyrrole (1-8)

A suspension of 1.75 g (5.6 mmol) 1-7 in 15 mL of EtOH and 10 mL of 3 M NaOH was heated at 60° C. for 3 h, cooled to room temperature and dumped into a separatory funnel with EtOAc and brine. The layers were separated, the aqueous phase was extracted twice with EtOAc, the combined organic phases were washed twice with brine, dried over Na$_2$SO$_4$, and concentrated to provide a white solid. To this flask was added 30 mL of CH$_2$Cl$_2$, 1.5 g (22.3 mmol) of imidazole and 1.76 g (11.7 mmol) of TBSCl, and the resultant suspension was stirred overnight. The reaction was diluted with CH$_2$Cl$_2$, washed twice with water, dried over Na$_2$SO$_4$, concentrated, and the residue purified by silica gel chromatography with EtOAc/hexanes to provide 1-8 as a white solid. Data for 1-8: $^1$HNMR (500 MHz, CDCl$_3$) δ 7.6-7.3 (m, 5H), 7.1-6.9 (m, 3H), 6.75 (s, 1H), 4.25 (d, 1H), 4.1 (d, 1H), 3.95 (d, 1H), 3.75 (d, 1H), 0.9 (s, 9H), 0.1 (s, 3H), 0.05 (s, 3H) ppm.

Step 6: Enantiomeric Resolution of Intermediate 1-8

Resolution of the enantiomers was carried out chromatographically using a Chiralpak AD® 10×50 cm column with 1% isopropanol in hexanes (with 0.1% diethylamine) at 150 mL/min. Analytical HPLC analysis of the eluent on a 4×250 mm Chiralpak AD® column with 1% isopropanol in hexanes (with 0.1% diethylamine) at 1 mL/min indicated that first eluting, active enantiomer has R$_t$=5.5 min and the second enantiomer has R$_t$=6.9 min.

Step 7: Carbamoyl chloride 1-9

To a solution of 1.95 g (6.6 mmol) of triphosgene in 25 mL of TBF at 0° C. was added a solution of 1.31 g (3.3 mmol) of the first eluting enantiomer of 1-8 and 915 μL (6.6 mmol) of triethylamine in 10 mL of THF. The ice bath was removed and the reaction was allowed to warm to room temperature and stir for 3 h. The reaction was then partitioned between water and EtOAc, the layers were separated, dried over Na$_2$SO$_4$, and concentrated to provide 1-9 as a brown oil. Data for 1-9:

HRMS (ES) calc'd M+H for C$_{24}$H$_{28}$ClF$_2$NO$_2$Si: 464.1619. Found: 464.1625.

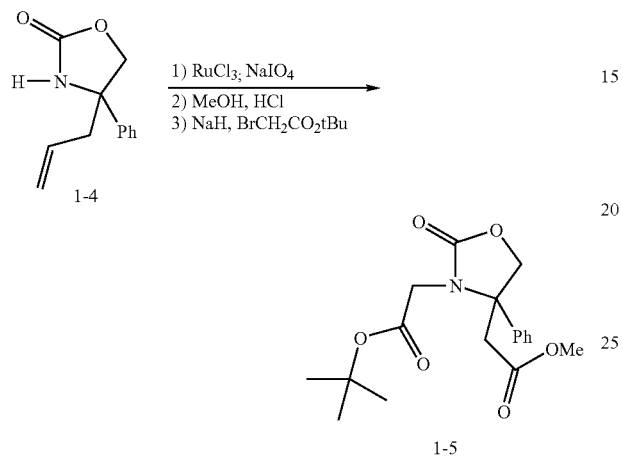

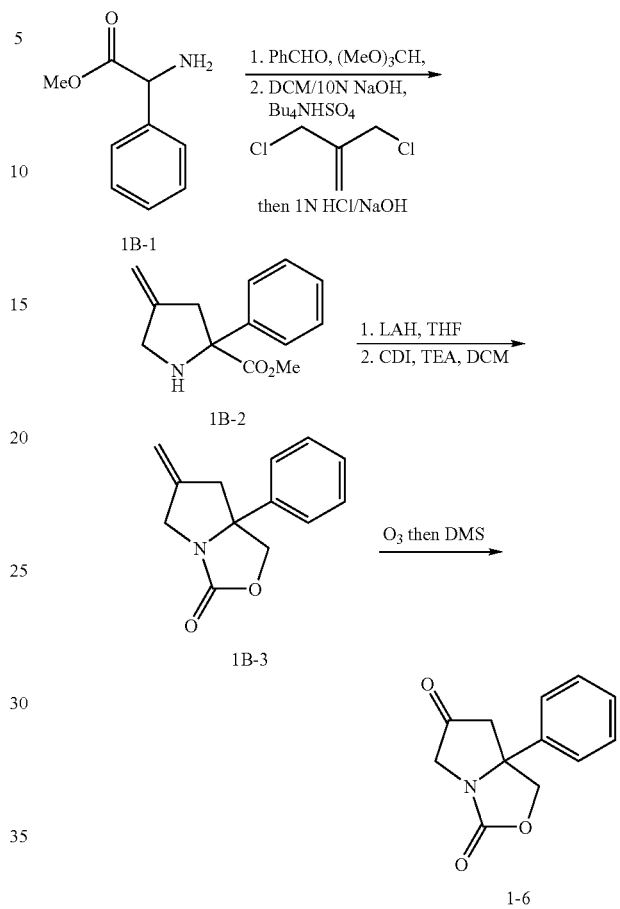

Alternate Synthesis to Diester 1-5

To a biphasic mixture of 14.8 g (73 mmol) of 1-4 and 110 mL of CH$_2$Cl$_2$, 110 mL of CH$_3$CN, and 320 mL of water was added approximately 200 mg of ruthenium(III) chloride hydrate. Sodium periodate (85.6 g, 400 mmol) was then added portion-wise over 1 h with rapid stirring. After the addition was complete, the reaction was allowed to stir for 4 h more at room temperature. The mixture was diluted with 500 mL of water and 1.5 L of EtOAc, and the solids were removed by filtration. The filtrate was placed in a separatory funnel, the phases separated, the aqueous phase extracted twice with EtOAc, the combined organic phases washed twice with brine, and dried over Na$_2$SO$_4$. Following concentration, the dark brown solid was dissolved in 250 mL of MeOH and HCl(g) was slowly passed through the solution at a rate so as not to increase the temperature of the solution above 35° C. After 5 min, the reaction was capped and allowed to stir at room temperature overnight. The volatiles were then removed on a rotary evaporator, and the residue was purified by silica gel chromatography with EtOAc/hexanes to provide 13.6 g (58 mmol) of the methyl ester as a viscous oil. This residue was then dissolved in 200 mL of ThF, cooled to 0° C., and 10.3 mL (70 mmol) of tert-butyl bromoacetate was added, followed by 2.8 g of NaH (70 mmol of a 60% suspension). After the mixture was allowed to warm to room temperature and stir overnight, it was quenched with a saturated NH$_4$Cl solution, and extracted twice with EtOAc. The combined organic layers were then washed with brine, dried over Na$_2$SO$_4$, concentrated, and the residue purified by silica gel chromatography with EtOAc/hexanes to provide 1-5 as a colorless oil. Data for 1-5: $^1$HNMR (500 MHz, CDCl$_3$) δ 7.4-7.3 (m, 5H), 4.65 (d, 1H), 4.55 (d, 1H), 3.9 (d, 1H), 3.65 (s, 3H), 3.5 (d, 1H), 3.35 (d, 1H), 3.2 (d, 1H), 1.4 (s, 9H) ppm. HRMS (ES) calc'd M+Na for C$_{18}$H23NO$_6$: 372.1423. Found: 372.1412.

Step 1: Methyl 4-methylene-2-phenylprolinate (1B-2)

An aqueous solution (300 mL) of phenyl glycine methyl ester-HCl (100 g) was neutralized to pH 8 with 10N NaOH. The aqueous solution was extracted with EtOAc (3×200 mL). The combined organic extracts were dried over MgSO$_4$, filtered, and concentrated. The residue (56.7 g, 344 mmol) was dissolved in trimethylorthoformate (100 mL) and treated with benzaldehyde (34.9 mL, 36.4 g, 344 mmol). After stirring for 2 h, the reaction was diluted with Et$_2$O (200 mL) and washed with water (3×50 mL). The organic solution was dried over MgSO$_4$, filtered, and concentrated. A portion of the imine residue (26.8 g, 100 mmol) was dissolved in dichloromethane (240 mL) and treated with 160 mL of 10N NaOH, methallyl dichloride (50.0 g, 400 mmol), and Bu$_4$NHSO$_4$ (3.59 g). After stirring for 10 h at rt, the reaction was diluted with dichloromethane and the organic solution separated, dried over MgSO$_4$, filtered, and concentrated. The residue was redissolved in Et$_2$O/1N HCl (200 mL/200 mL) and stirred for 2 h. The aqueous phase was separated and neutralized with 10N NaOH (to pH 8). The aqueous mixture was extracted with EtOAc (3×200 mL). The combined organic solutions were dried over MgSO$_4$, filtered and concentrated. The residue was dissolved in water and neutralized (to pH 8). Extraction of this mixture with EtOAc (×3) followed by drying over MgSO$_4$, filtratration, and concentration provided crude 1B-2. Purification of this residue by flash chromatography (SiO$_2$; 30% EtOAc/hexanes) provided pure 1B-2.

Data for 1B-2: $^1$HNMR (500 MHz, CDCl$_3$) δ 7.51 (m, 2H), 7.42 (m, 3H), 5.03 (s, 1H), 4.95 (s, 1H), 3.71 (m, 5H), 3.41 (rn, 1H), 2.80 (m, 1H) ppm.

Step 2: 7a-Phenyldihydro-1H-pyrrolo[1,2-c][1.3]oxazole-3,6(5H)-dione (1-6)

A suspension of LiAlH$_4$ (7.14 g, 188 mmol) in THF (500 mL) was cooled to 0° C. and treated with a solution of ester 1B-2 (10.2 g, 47 mmol) in THF (50 mL) over 20 min. After stirring for 30 min at 0° C., the reaction was cautiously quenched by the addition of water (7.1 mL), 15% aq NaOH (7.1 mL), and H$_2$O (21.3 mL). Solid Na$_2$SO$_4$ was added and the mixture stirred for 40 min. The mixture was filtered and concentrated. The residue (8.2 g, 43.3 mmol) was dissolved in dichloromethane (300 mL) and treated with triethylamine (9.0 mL, 6.5 g, 65.0 mmol) and carbonyldiimidazole (9.14 g, 56.4 mmol). After stirring for 48 h at rt, the reaction was diluted with dichloromethane and washed with 1N HCl and brine. The organic solution was concentrated and not further purified. A solution of the residue 1B-3 (9.2 g, 42.8 mmol) in dichloromethane (200 mL) was cooled to –78° C. and ozone was passed through the solution until a blue color persisted. The solution was purged and treated with dimethylsulfide (35 mL). After gradual warming to rt overnight, the solution was concentrated to a yellow solid. Trituration of this solid with Et$_2$O provided pure 1-6. Data for 1-6: $^1$HNMR (500 MHz, CDCl3) δ 8 7.5-7.3 (m, 5H), 4.7 (d, 1H), 4.3 (d, 1H), 4.2 (d, 1H), 3.5 (d, 1H), 3.1 (d, 1H), 2.95 (d, 1H), 2.9 (d, 1H) ppm The compounds of the instant invention are prepared by reacting compound 1-9 with reagents (prepared as illustrated in Schemes B and D-F) as shown in Schemes C and G-O above.

SCHEME 2

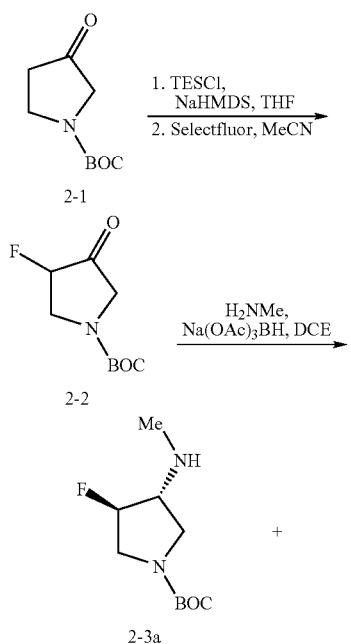

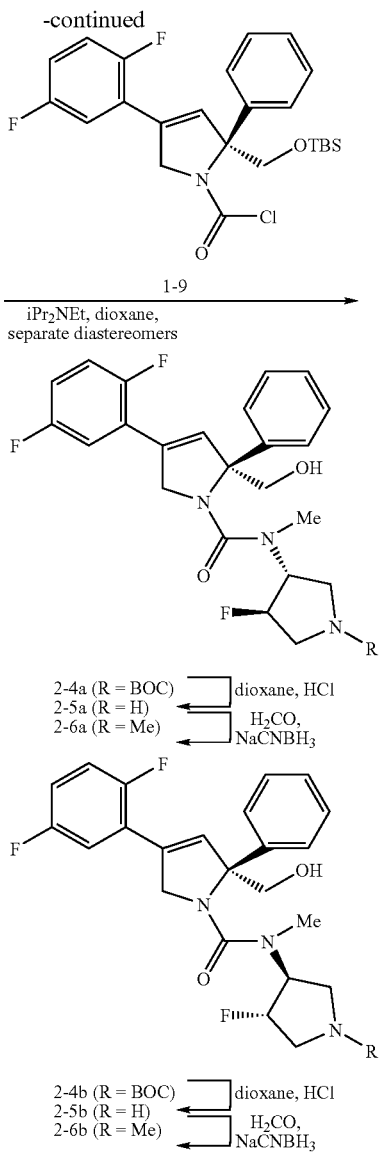

Step 1: (±)-N-BOC-trans-3-fluoro-4(methylamnino)pyrrolidine 2-3

A cooled solution (–78° C.) of N-BOC-3-pyrrolidinone (1.0 g, 5.41 mmol) in THF (50 mL) was treated with a solution of NaHMDS (7.03 mL of a 1M soln in THF). After stirring for 30 min, the solution was treated with chlorotriethylsilane (1.18 mL, 7.03 mmol). The reaction was stirred for 1 hr at –78° C., warmed to 0° C., diluted with 1:1 brine/water and hexanes. The mixture was extracted with EtOAc. The organic solution was dried over Na$_2$SO$_4$, filtered, and concentrated. The residue was not further purified. A solution of the 3-fluoro-N-BOC-pyrrolidinone (0.31 g, 1.53 mmol) in dichloroethane (10 mL) was treated with methylarnine (1.53 mL of a 2M soln in THF) and Na(OAc)$_3$BH (0.49 g, 2.3 mmol). After stirring for 12 h at room temperature, the reaction was diluted with EtOAc and washed with satd NaHCO$_3$. The organic solution was dried over MgSO$_4$, filtered, and concentrated. The residue was purified by flash chromatography (SiO$_2$; 80% CHCl$_3$/10% MeOH/10% EtOAc) to provide racemic 2-3. Data for 2-3: ¹HNMR (500 MHz, CDCl₃) δ 5.11 (br d, J=55 Hz, 1H), 3.85-3.62 (m, 2H), 3.51 (m, 1H), 3.20 (m, 1H), 3.03 (m, 1H), 2.50 (s, 3H), 1.46 (s, 9H) ppm.

Step 2: (2S)-4-2,5-Difluorophenyl)-N-[(3R,4R)-4-fluoropyrrolidin-3-yl]-2-hydroxymethyl)N-phenyl-2,5-dihydro-1H-pyrrole-1-carboxamide 2-5a and (2S)-4-2,5-Difluorophenyl)-N-[(3S,4S)-4-fluoropyrrolidin-3-yl]-2-(hydroxymethyl)N-phenyl-2,5-dihydro-1H-pyrrole-1-carboxamide 2-5b A solution of the the carbamoyl chloride 1-9 (0.24 g, 0.52 mmol), fluoropyrrolidine 2-3 (0.114 g, 0.52 mmol), and iPr₂NEt (0.177 mL, 1.04 mmol) in dioxane (5 mL) was heated at 90° C. for 12 h. The reaction was cooled to room temperature, diluted with EtOAc and washed with satd aq NH₄Cl and brine. The organic solution was dried over MgSO₄, filtered, and concentrated. The residue was purified by flash chromatography (SiO₂; 10% EtOAc/hexanes) to provide diastereomers 2-4a and 2-4b. Diastereomer 2-4a (0.1 g) was dissolved in dioxane (2 mL) and treated with HCl (2 mL of a 4M soln in dioxane). After stirring for 2 h, the reaction was neutized with satd aq NaHCO₃ and extracted with EtOAc. The organic solution was dried over MgSO₄, filtered, and concentrated. Flash chromatography on SiO₂ (95/2.5/2.5 dichloromethane/NH₄OH/MeOH) afforded pure first eluting 2-5a. 2-5b was prepared in a similar fashion.

Data for 2-5a: ¹HNMR (500 MHz, CDCl₃) δ 7.40-7.35 (m, 5H), 7.07-6.96 (m, 3H), 6.30 (s, 1H), 5.34-5.23 (br d, J=55 Hz, 1H), 4.86 (d, J=14 Hz, 1H), 4.75 (d, J=14 Hz, 1H), 4.52 (m, 1H), 4.05 (m, 2H), 3.27 (m, 3H1), 3.08 (s, 3H) ppm.

Data for 2-5b: ¹HNMR (500 MHz, CDCl₃) δ 7.41-7.37 (m, 5H), 7.09-6.96 (m, 3H), 6.32 (s, 1H), 5.36-5.23 (dt, J=55, 4 Hz, 1H), 4.90 (d, J=15 Hz, 1H), 4.67 (d, J=15 Hz, 1H), 4.45 (d, J=12H, 1H), 4.03 (m, 2H), 3.29 (m, 3H), 3.18 (s, 3H) ppm.

Step 3: (2S)-4-(2,5-Difluorophenyl)-N-[(3R,4R)-4-fluoro-1-methylpyrrolidin-3-yl]-2-(hydroxymethyl)N-phenyl-2,5-dhydro-1H-pyrrole-1-carboxamide 2-6a and (2S)-4-2,5-Difluorophenyl)-N-[(3S,4S)-4-fluoro-1-methylpyrrolidin-3-yl]-2-(hydroxymethyl)N-phenyl-2,5-dihydro-1H-pyrrole-1-carboxamide 2-6b A solution of amine 2-5a (0.050 g, 0.116 mmol), aqueous formaldehyde (0.030 mL, 0.348 mmol), NaCNBH₃ (0.024 g, 0.348 mmol), AcOH (10 µL) in MeOH (4.0 mL) was stirred at rt for 12 h. The reaction was treated with satd aq NaHCO₃ (30 uL) and concentrated. The reaction was purified by flash chromatography (SiO₂; 95/2.5/2.5 dichloromethane/NH₄OH/MeOH) to provide 2-6a. 2-6b was prepared in a similar fashion.

Data for 2-6a: ¹HNMR (500 MHz, CDCl₃) δ 7.41-7.36 (ma, 4H), 7.29-7.26 (m, 1H), 7.08-6.95 (m, 3H), 6.29 (s, 1H), 5.31-5.18 (br d, J=55 Hz, 1H), 4.89-4.86 (d, J=14 Hz, 1H), 4.78-4.75 (d, J=14 Hz, 1H), 4.52 (d, J=12 Hz, 1H), 4.37-4.28 (m, 1H), 4.05 (d, J=12 Hz, 1H), 3.10 (s, 3H), 2.99-2.81 (m, 4H), 2.43 (s, 3H) ppm.

Data for 2-6b: ¹HNMR (500 MHz, CDCl₃) δ 7.39-7.26 (m, 5H), 7.08-6.96 (m, 3H), 6.33 (s, 1H), 5.35-5.22 (dt, J=54, 4.5 Hz, 1H), 4.94-4.91 (d, J=14 Hz, 1H), 4.65-4.62 (d, J=14 Hz, 1H), 4.43-4.32 (m, 2H), 4.02-3.99 (d, J=13 Hz, 1H), 3.22 (s, 3H), 3.16-3.02 (m, 2H), 2.71-2.61 (m, 2H), 2.44 (s, 3H) ppm.

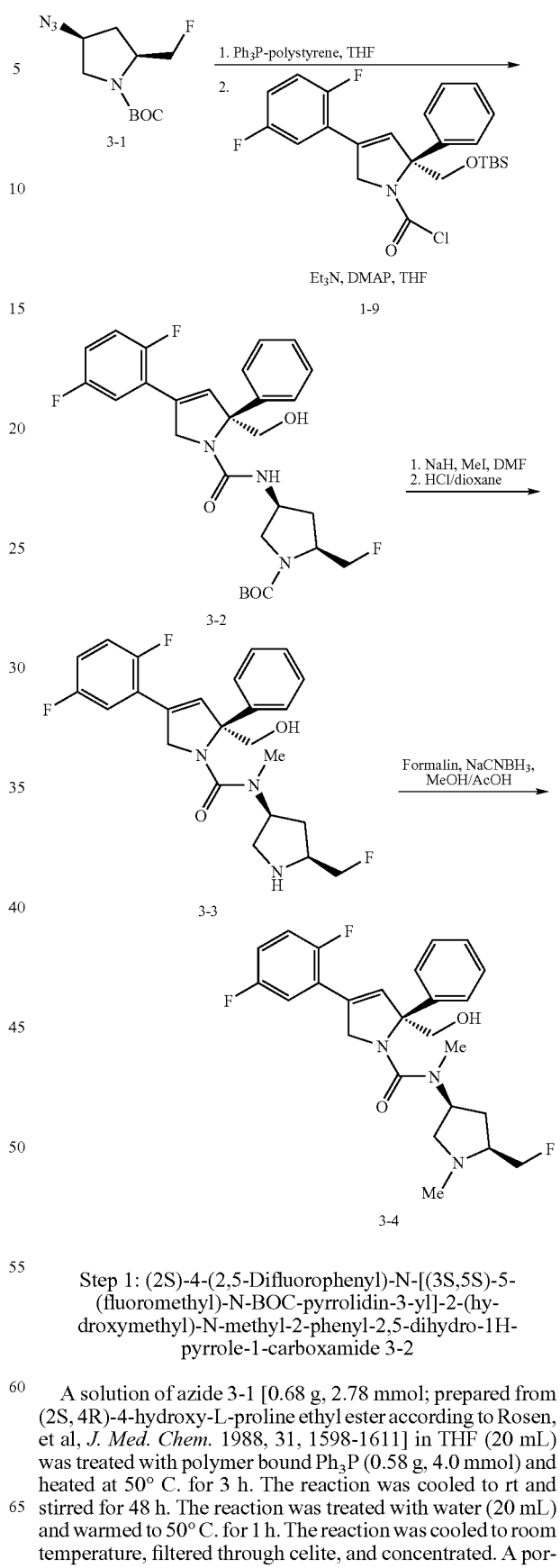

SCHEME 3

Step 1: (2S)-4-(2,5-Difluorophenyl)-N-[(3S,5S)-5-(fluoromethyl)-N-BOC-pyrrolidin-3-yl]-2-(hydroxymethyl)-N-methyl-2-phenyl-2,5-dihydro-1H-pyrrole-1-carboxamide 3-2

A solution of azide 3-1 [0.68 g, 2.78 mmol; prepared from (2S, 4R)-4-hydroxy-L-proline ethyl ester according to Rosen, et al, J. Med. Chem. 1988, 31, 1598-1611] in THF (20 mL) was treated with polymer bound Ph₃P (0.58 g, 4.0 mmol) and heated at 50° C. for 3 h. The reaction was cooled to rt and stirred for 48 h. The reaction was treated with water (20 mL) and warmed to 50° C. for 1 h. The reaction was cooled to room temperature, filtered through celite, and concentrated. A portion of the residue (0.103 g, 0.474 mmol) was treated with carbamoyl chloride 1-9 (0.22 g, 0.474 mmol), triethylamine (0.129 mL, 0.948 mmol), and a catalytic amount of DMAP. The reaction was stirred for 48 h at room temperature. The reaction was diluted with EtOAc and washed with 10% citric acid, satd aq NaHCO$_3$, and brine. The organic solution was dried over MgSO$_4$, filtered and concentrated. The residue was purified by chromatography on SiO$_2$ (gradient 100% hexanes to 50% EtOAc/hexanes over 45 min) provided 3-2 as a white solid. LRMS M+H=646.4.

Step 2: (2S)-4-(2,5-Difluorophenyl)-N-[(3S,5S)-5-(fluoromethyl)-pyrrolidin-3-yl]-2-(hydroxymethyl)-N-methyl-2-phenyl-2,5-dihydro-1H-pyrrole-1-carboxamide 3-3

A solution of 3-2 (0.18 g, 0.279 mmol) in DMF (3 mL) at 0° C was treated with NaH (0.009 g, 0.362 mmol) and iodomethane (0.023 mL, 0.362 mol). The reaction was stirred for 12 h with gradual warming to rt A second portion (0.3 eq) of both iodomethane and NaH were added. After stirring for another 3 h, the reaction was diluted with EtOAc, washed with water, 10% citric acid, satd aq NaHCO$_3$, and brine. The organic solution was dried over MgSO$_4$, filtered and concentrated. The residue was purified by chromatography (SiO$_2$; 100% hexanes to 3/1 hexanes/EtOAc over 45 min). This material (0.150 g, 0.227 mmol) was dissolved in EtOAc (1.2 mL) and treated with a solution of HCl in dioxane (4M, 1.2 mL). After stirring for 2 h, the reaction was diluted with EtOAc and satd aq NaHCO$_3$ (~3 mL) was added. The mixture was concentrated and rediluted with 15% Na$_2$CO$_3$. The mixture was extracted with 2/1 CHCl$_3$: EtOH (×3) and the combined organic solution was concentrated. The residue was diluted with dichloromethane washed with brine, dried over Na$_2$SO$_4$, filtered and concentrated to provide 3-3 Data for 3-3: $^1$HNMR (500 MHz, CD$_3$OD) δ 7.38-7.31 (m, 4H), 7.25-7.22 (m, 2H), 7.19-7.14 (m, 1H), 7.10-7.06 (m, 1H), 6.31 (s, 1H), 4.95 (d, J=14 Hz, 1H), 4.77 (d, J=14 Hz, 1H), 4.61 (d, J=11.2 Hz, 1H), 4.51 (m, 1H), 4.43 (m, 1H), 4.34 (m, 1H), 4.20 (d, J=11 Hz, 1H), 4.11 (m, 1H), 3.08 (m, 1H), 2.09 (m, 4H), 2.02 (m, 1H), 1.56 (m, 1H) ppm.

Step 3: (2S)-4-2,5-Difluorophenyl)-N-[(3S,5S)-5-(fluoromethyl)-1-methylpyrroldin-3-yl]-2-(hydroxyethyl)-N-methyl-2-phenyl-2,5-dihydro-1H-pyrrole-1-carboxamide 3-4

A solution of 3-3 (0.90 g, 0.202 mmol) in MeOH (2 mL) was treated with AcOH (20 uL), aqueous formaldehyde (0.018 g, 0.606 mmol), and NaCNBH$_3$ (0.038 g 0.606 mmol). After stirring for 1 h at room temperature, the reaction was treated with satd aqueous NaHCO$_3$, and extracted with EtOAc. The combined organic solutions were washed with brine, dried over MgSO$_4$, filtered and concentrated. The residue was purified by chromatography (SiO$_2$, 100% EtOAc to 10% MeOH in EtOAc) to provide 34.

Data for 3-4: $^1$HNMR (500 MHz, CDCl$_3$) δ 7.35 (m, 5H), 6.96 (m, 3H), 6.27 (s, 1H), 5.39 (m, 1H), 4.85 (d, J=15 Hz, 1H), 4.53 (m, 4H), 3.98(dd, J=12, 3.7 Hz, 1H), 3.14 (dd, J=11, 2.2 Hz, 1H), 3.07 (s, 3H), 2.53 (mn, 1H), 2.42 (m, 4H), 1.70 (m, 1H) ppm.

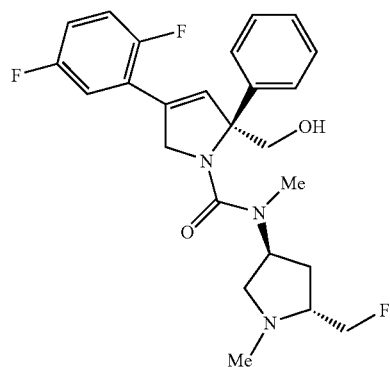

3-5

(2S)-4-(2,5-Difluorophenyl)-N-[(3S,5R)-5-(fluoromethyl)-1-methylpyrrolidin-3-yl]-2-(hydroxymethyl)-N-methyl-2-phenyl-2,5-dihydro-1H-pyrrole-1-carboxamide 3-5

Compound 3-5 was prepared by sequence analogous to Scheme 3 beginning with (2R, 4R-)4 -hydroxy-D-proline methyl ester. Data for 3-5: $^1$HNMR (500 MHz, CDCl$_3$) δ 7.37 (mn, 5H), 6.97 (m, 3H), 6.26 (s, 1H), 5.23 (d, J=5.5 Hz, 1H), 4.84 (d, J=14 Hz, 1H), 4.63 (d, J=14 Hz, 1H), 4.45 (m, 2H), 4.37 (m, 2H), 4.01 (dd, J=11, 3 Hz, 1H), 3.24 (m, 1H), 2.93 (s, 3H), 2.76 (m, 1H), 2.51 (m, 1H), 2.44 (s, 3H) ppm.

---

What is claimed is:

1. The compound of the formula IV:

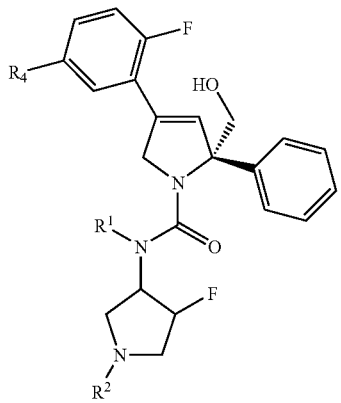

or a pharmaceutically acceptable salt or stereoisomer thereof, wherein:
   $R^1$ and $R^2$ are independently selected from: H and ($C_1$-$C_6$) alkyl; and
   $R^4$ is halo.

2. A compound selected from:
   (2S)-4-(2,5-Difluorophenyl)-N-[(3R,4R)-4-fluoropyrrolidin-3-yl]-2-(hydroxymethyl)2-phenyl-2,5-dihydro-1H-pyrrole-1-carboxamide,
   (2S)-4-(2,5-Difluorophenyl)-N-[(3S,4S)-4-fluoropyrrolidin-3-yl]-2-hydroxymethyl)2-phenyl-2,5-dihydro-1H-pyrrole-1-carboxamide,
   (2S)-4-(2,5-Difluorophenyl)-N-[(3R,4R)-4-fluoro-1-methylpyrrolidin-3-yl]-2-(hydroxymethyl)2-phenyl-2,5-dihydro-1H-pyrrole-1-carboxamide,
   (2S)4-2,5-Difluorophenyl)-N-[(3S,4S)-4-fluoro-1-methylpyrrolidin-3-yl]-2-(hydroxymethyl)2-phenyl-2,5-dihydro-1H-pyrrole-1-carboxamide,
   (2S)-4-2,5-Difluorophenyl)-N-[(3S,5S)-5-(fluoromethyl)-pyrrolidin-3-yl]-2-(hydroxymethyl)-N-methyl-2-phenyl-2,5dihydro-1H-pyrrole-1-carboxaride,
   (2S)-4-2,5-Difluorophenyl)-N-[(3S,5S)-5-fluoromethyl)-1-methylpyrrolidin-3-yl]-2-(hydroxymethyl)-N-methyl-2-phenyl-2,5-dihydro-1H-pyrrole-1-carboxamide,
   (2S)-4-2,5-Difluorophenyl)-N-[(3S,5R)-5-(fluoromethyl)-pyrrolidin-3-yl]-2-(hydroxymethyl)-N-methyl-2-phenyl-2,5-dihydro-1H-pyrrole-1-carboxamide
   (2S)-4-2,5-Difluorophenyl)-N-[(3S,5R)-5-(fluoromethyl)-1-methylpyrrolidin-3-yl]-2-(hydroxymethyl)-N-methyl-2-phenyl-2,5-dihydro-1H-pyrrole-1-carboxamide, or a pharmaceutically acceptable salt or stereoisomer thereof.

3. A pharmaceutical composition that is comprised of a compound in accordance with claim 1 and a pharmaceutically acceptable carrier.

* * * * *

SEQUENCE LISTING

```
<160> NUMBER OF SEQ ID NOS: 2

<210> SEQ ID NO 1
<211> LENGTH: 42
<212> TYPE: DNA
<213> ORGANISM: Artificial Sequence
<220> FEATURE:
<223> OTHER INFORMATION: Completely Synthetic Nucleotide Sequence

<400> SEQUENCE: 1
gcaacgatta atatggcgtc gcagccaaat tcgtctgcga ag                       42

<210> SEQ ID NO 2
```

```
<211> LENGTH: 60
<212> TYPE: DNA
<213> ORGANISM: Artificial Sequence
<220> FEATURE:
<223> OTHER INFORMATION: Completely Synthetic Nucleotide Sequence

<400> SEQUENCE: 2
gcaacgctcg agtcagtgat gatggtggtg atgctgattc acttcaggct tattcaatat      60
```